(12) United States Patent
Minning et al.

(10) Patent No.: US 7,507,569 B2
(45) Date of Patent: Mar. 24, 2009

(54) VARIANT SUBTILISIN ENZYMES (SUBTILASES)

(75) Inventors: Stefan Minning, Frederiksberg C (DK); Jurgen Carsten Franz Knotzel, Copenhagen O (DK); Niels Henrik Sorensen, Skaevinge (DK); Jon E. Ness, Redwood City, CA (US); Mark D. Welch, Freemont, CA (US); Lorraine J. Giver, Sunnyvale, CA (US); Joel Cherry, Davis, CA (US); Torben Vedel Borchert, Birkeroed (DK); Jeremy Minshull, Los Altos, CA (US)

(73) Assignees: Novozymes A/S, Bagsvaerd (DK); Maxygen Inc., Redwood City, CA (US)

( * ) Notice: Subject to any disclaimer, the term of this patent is extended or adjusted under 35 U.S.C. 154(b) by 247 days.

(21) Appl. No.: 10/555,484

(22) PCT Filed: May 6, 2004

(86) PCT No.: PCT/DK2004/000312

§ 371 (c)(1),
(2), (4) Date: Mar. 16, 2006

(87) PCT Pub. No.: WO2004/099401

PCT Pub. Date: Nov. 18, 2004

(65) Prior Publication Data

US 2007/0015677 A1    Jan. 18, 2007

Related U.S. Application Data

(60) Provisional application No. 60/470,360, filed on May 14, 2003.

(30) Foreign Application Priority Data

May 7, 2003    (DK) .................... 2003 00690

(51) Int. Cl.
  *C12N 9/54* (2006.01)
  *C12N 15/57* (2006.01)
  *C12N 15/74* (2006.01)
  *C11D 3/386* (2006.01)

(52) U.S. Cl. .................. 435/221; 435/69.1; 435/252.3; 435/320.1; 435/264; 435/263; 510/300; 510/111; 510/392; 536/23.2

(58) Field of Classification Search .................. None
See application file for complete search history.

(56) References Cited

U.S. PATENT DOCUMENTS 4,914,031 A * 4/1990 Zukowski et al. ........... 435/222

(Continued)

FOREIGN PATENT DOCUMENTS

EP    0 130 756    1/1985

(Continued)

OTHER PUBLICATIONS

Russell et al., J. Mol. Biol., vol. 193, pp. 803-813 (1987).

(Continued)

*Primary Examiner*—Rebecca E Prouty
*Assistant Examiner*—William W Moore
(74) *Attorney, Agent, or Firm*—Elias J. Lambiris; Kristin J. McNamara

(57) ABSTRACT

Novel subtilases having an improved wash performance on egg stains are disclosed. These subtilases are useful exhibiting excellent or improved wash performance on egg stains when used in e.g. cleaning or detergent compositions, such as laundry detergent compositions and dish wash compositions, including automatic dish wash compositions.

13 Claims, 4 Drawing Sheets

```
No:             260           270      275 a)    ENTTTKLGDSFYYGKGLINVQAAAQ b)    KNTATSLGSTNLYGSGLVNAEAATR c)    KNTATSLGSTNLYGSGLVNAEAATR d)    KNTATSLGSTNLYGSGLVNAEAATR
```

U.S. PATENT DOCUMENTS

| | | | | |
|---|---|---|---|---|
| 4,990,452 A * | 2/1991 | Bryan et al. | | 435/222 |
| 5,260,207 A * | 11/1993 | Pantoliano et al. | | 435/221 |
| 5,340,735 A * | 8/1994 | Christianson et al. | | 435/221 |
| 5,397,705 A * | 3/1995 | Zukowski et al. | | 435/222 |
| 5,500,364 A * | 3/1996 | Christianson et al. | | 435/221 |
| 5,543,302 A | 8/1996 | Boguslawski et al. | | |
| 5,665,587 A * | 9/1997 | Aaslyng et al. | | 435/221 |
| 5,677,272 A * | 10/1997 | Ghosh et al. | | 510/306 |
| 5,679,630 A * | 10/1997 | Baeck et al. | | 510/305 |
| 5,837,517 A * | 11/1998 | Sierkstra et al. | | 435/221 |
| 6,586,221 B2 * | 7/2003 | Graycar et al. | | 435/219 |
| 6,777,218 B1 * | 8/2004 | Mikkelsen et al. | | 435/220 |
| 6,902,922 B2 * | 6/2005 | Ness et al. | | 435/219 |
| 7,262,042 B2 * | 8/2007 | Weber et al. | | 435/212 |
| 2004/0197894 A1 * | 10/2004 | Fano et al. | | 435/234 |

FOREIGN PATENT DOCUMENTS

| | | |
|---|---|---|
| EP | 0 214 435 | 3/1987 |
| EP | 0 260 105 | 3/1988 |
| EP | 0 525 610 | 2/1993 |
| EP | 0 251 446 | 12/1994 |
| WO | WO 87/04461 | 7/1987 |
| WO | WO 87/05050 | 8/1987 |
| WO | WO 88/08028 | 10/1988 |
| WO | WO 88/08033 | 10/1988 |
| WO | WO 89/06279 | 7/1989 |
| WO | WO 91/00345 | 1/1991 |
| WO | WO 94/02618 | 2/1994 |
| WO | WO 95/27049 | 10/1995 |
| WO | WO 95/29979 | 11/1995 |
| WO | WO 95/30010 | 11/1995 |
| WO | WO 95/30011 | 11/1995 |
| WO | WO 01/68821 | 9/2001 |
| WO | WO 01/75087 | 10/2001 |
| WO | WO 02/42740 | 5/2002 |

OTHER PUBLICATIONS

Thomas et al., Nature, vol. 318, pp. 375-376 (Nov. 28, 1985).
Russell et al., Nature, vol. 328, pp. 496-500 (Aug. 6, 1987).
Philip N. Bryan, Biochimica et Biophysica Acta, vol. 1543, pp. 203-222 (2000).
R. Gupta et al., Applied Microbiol Biotechnol, vol. 59, pp. 15-32 (2002).

* cited by examiner

| No: | 260 | 270 | 275 | a) ENTTTKLGDSFYYGKGLINVQAAAQ b) KNTATSLGSTNLYGSGLVNAEAATR c) KNTATSLGSTNLYGSGLVNAEAATR d) KNTATSLGSTNLYGSGLVNAEAATR

Fig. 1

Enzyme concentrations (nM):

| Wash Unit | Enzyme 2 | | | | | | BACK | Enzyme 4 | | | | | | |
|---|---|---|---|---|---|---|---|---|---|---|---|---|---|---|
| | 1 | 2 | 3 | 4 | 5 | 6 | | 1 | 2 | 3 | 4 | 5 | 6 | |
| D | 0 | 20 | 40 | 75 | 100 | 160 | | 0 | 20 | 40 | 75 | 100 | 160 | H |
| C | 0 | 20 | 40 | 75 | 100 | 160 | | 0 | 20 | 40 | 75 | 100 | 160 | G |
| | | | REF. | | | | | | | | Enz3 | | | |
| B | 0 | 20 | 40 | 75 | 100 | 160 | | 0 | 20 | 40 | 75 | 100 | 160 | F |
| A | 0 | 20 | 40 | 75 | 100 | 160 | | 0 | 20 | 40 | 75 | 100 | 160 | E |

FRONT

Soiling:

| Enzyme 2 | | | | | | BACK | Enzyme 4 | | | | | | |
|---|---|---|---|---|---|---|---|---|---|---|---|---|---|
| | 1 | 2 | 3 | 4 | 5 | 6 | | 1 | 2 | 3 | 4 | 5 | 6 |
| D | Egg yolk | Egg yolk | Egg yolk | Egg yolk | Egg yolk | Egg yolk | | Egg yolk | Egg yolk | Egg yolk | Egg yolk | Egg yolk | Egg yolk | H |
| C | Egg/milk | Egg/milk | Egg/milk | Egg/milk | Egg/milk | Egg/milk | | Egg/milk | Egg/milk | Egg/milk | Egg/milk | Egg/milk | Egg/milk | G |
| | | | REF. | | | | | | | | Enz3 | | | |
| B | Egg yolk | Egg yolk | Egg yolk | Egg yolk | Egg yolk | Egg yolk | | Egg yolk | Egg yolk | Egg yolk | Egg yolk | Egg yolk | Egg yolk | F |
| A | Egg/milk | Egg/milk | Egg/milk | Egg/milk | Egg/milk | Egg/milk | | Egg/milk | Egg/milk | Egg/milk | Egg/milk | Egg/milk | Egg/milk | E |

FRONT

Fig.2

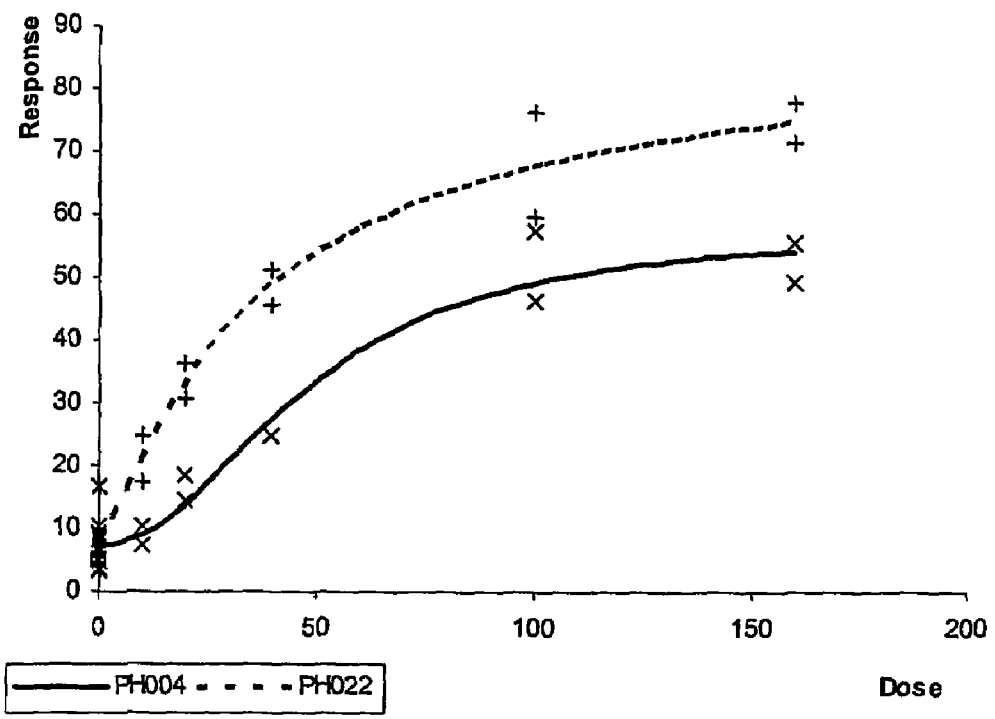
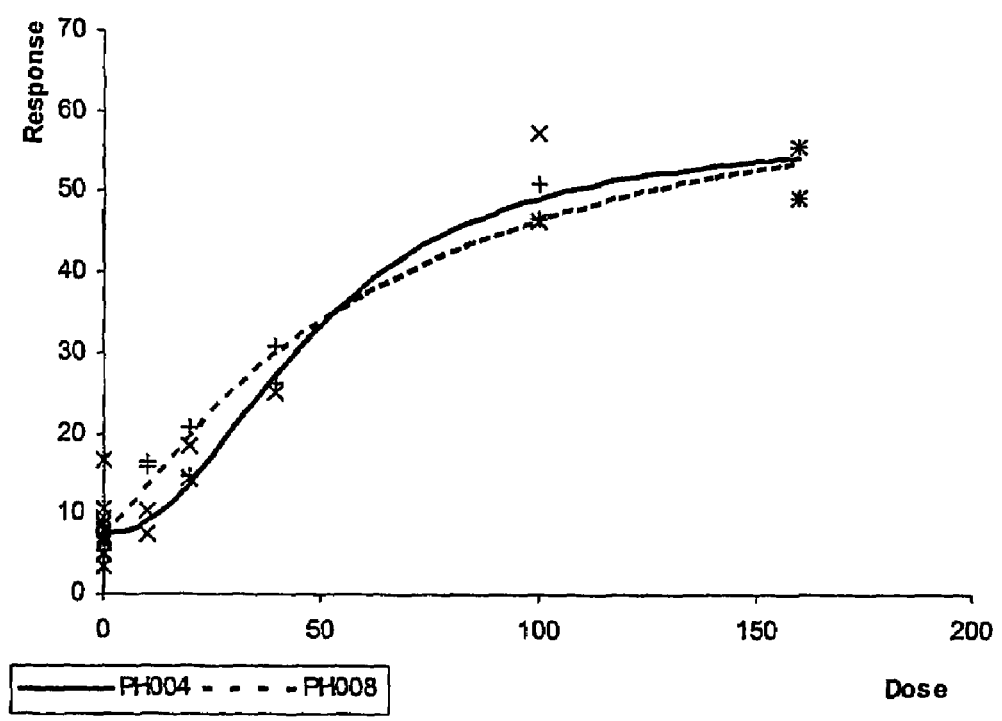
Fig. 3

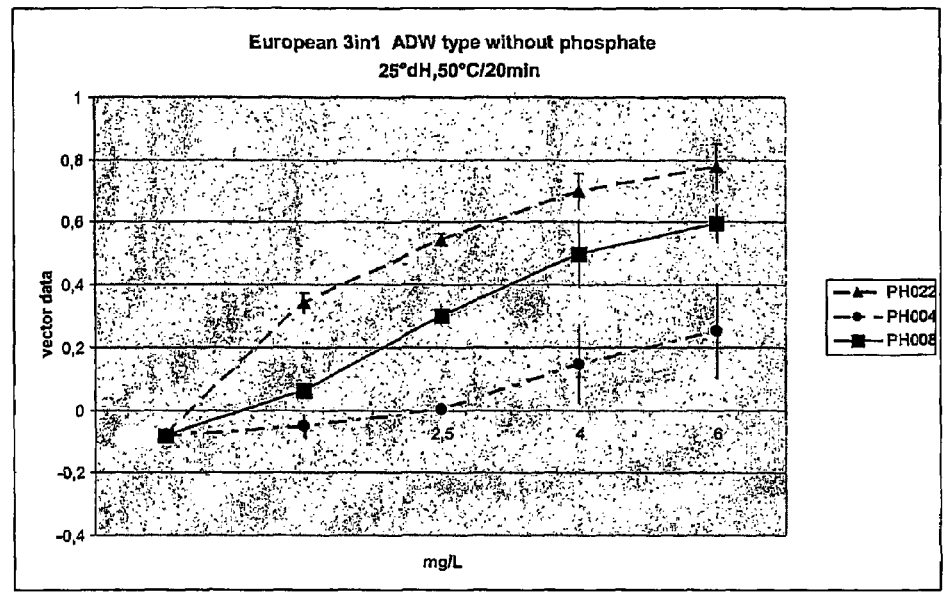
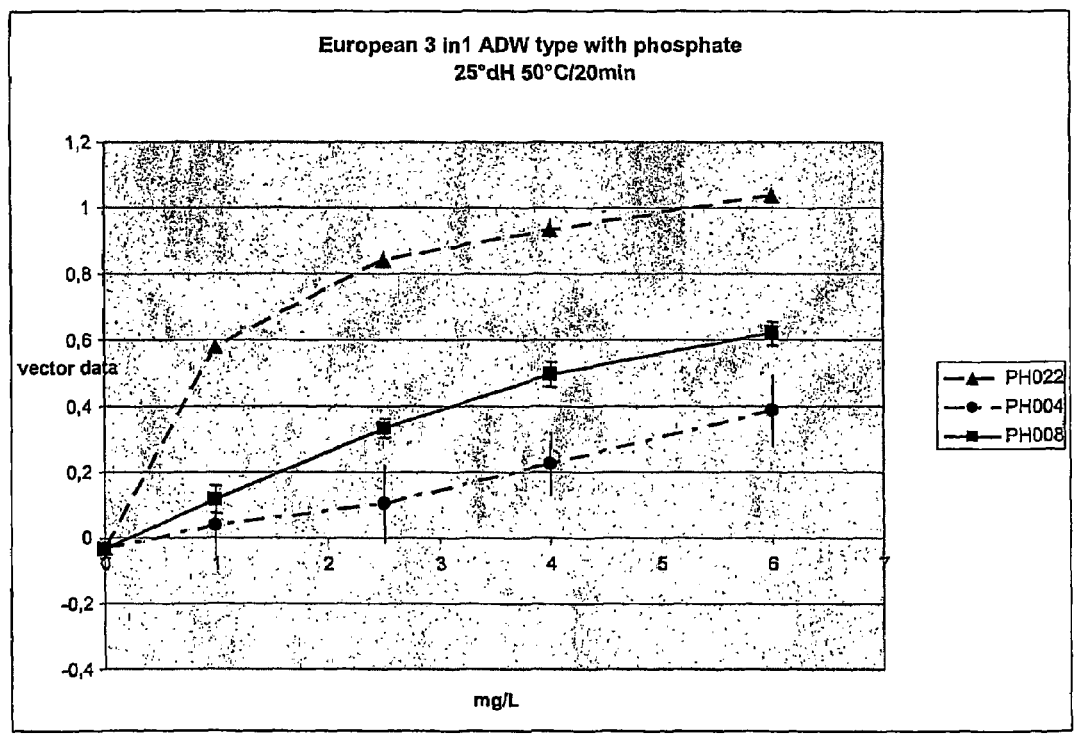
Fig. 4

VARIANT SUBTILISIN ENZYMES (SUBTILASES)

CROSS-REFERENCE TO RELATED APPLICATIONS

This application is a 35 U.S.C. 371 national application of PCT/DK2004/000312 filed May 6, 2004 which claims priority or the benefit under 35 U.S.C. 119 of Danish application no. PA 2003 00690 filed May 7, 2003 and U.S. provisional application No. 60/470,360 filed May 14, 2003, the contents of which are fully incorporated herein by reference.

TECHNICAL FIELD

The present invention relates to novel subtilases having an improved performance on soil, in particular egg stains. These subtilases are useful exhibiting excellent or improved performance on egg stains when used in e.g. cleaning or detergent compositions, such as laundry detergent compositions and dish wash compositions, including automatic dish wash compositions.

The present invention also relates to isolated polynucleotides encoding the subtilases, nucleic acid constructs, recombinant expression vectors, host cells comprising the nucleic acid construct, and methods for producing and using the subtilases of the invention. Further, the present invention relates to cleaning and detergent compositions comprising the subtilase enzymes of the invention as well as to use of such enzymes in detergent compositions and for removal of egg stains.

BACKGROUND OF THE INVENTION

In the detergent industry enzymes have for more than 30 years been implemented in washing formulations. Enzymes used in such formulations comprise proteases, lipases, amylases, cellulases, mannosidases as well as other enzymes or mixtures thereof. Commercially most important enzymes are proteases.

An increasing number of commercially used proteases is protein engineered variants of naturally occurring wild type proteases, e.g. DURAZYM® (Novozymes A/S), RELASE® (Novozymes A/S), MAXAPEM® (Gist-Brocades N.V.), PURAFECT® (Genencor International, Inc.).

Further, a number of protease variants is described in the art, such as in EP 130756 (GENENTECH) (corresponding to U.S. Re. Pat. No. 34,606 (GENENCOR)); EP 214435 (HENKEL); WO 87/04461 (AMGEN); WO 87105050 (GENEX); EP 260105 (GENENCOR); Thomas, Russell, and Fersht (1985) Nature 318 375-376; Thomas, Russell, and Fersht (1987) *J. Mol. Biol.* 193 803-813; Russel and Fersht Nature 328 496-500 (1987); WO 88/08028 (Genex); WO 88/08033 (Amgen); WO 95/27049 (SOLVAY S. A.); WO 95/30011 (PROCTER & GAMBLE COMPANY); WO 95/30010 (PROCTER & GAMBLE COMPANY); WO 95/29979 (PROCTER & GAMBLE COMPANY); U.S. Pat. No. 5,543,302 (SOLVAY S. A.); EP 251 446 (GENENCOR); WO 89/06279 (NOVOZYMES A/S); WO 91/00345 (NOVOZYMES A/S); EP 525 610 A1 (SOLVAY); WO 94/02618 (GIST-BROCADES N.V.).

Test method used for screening (AMSA) is described in WO 02/42740 (NOVOZYMES A/S).

WO 01/75087 (MAXYGEN, INC./NOVOZYMES A/S) describes subtilisin homologues that are improved for a variety of specific properties including thermal stability, activity at low temperature and alkaline stability.

WO 01/68821(NOVOZYMES A/S) describes subtilase enzymes, which are suitable for removal of egg stains from for example laundry and/or hard surfaces.

However, even though a number of useful proteases and protease variants have been described, there is still a need for further improvement of proteases or protease variants for a number of industrial uses.

In particular, the problem of removing egg stains from e.g. laundry or hard surfaces has been pronounced due to the fact that substances present in the egg white inhibit many serine proteases.

Therefore, an object of the present invention is to provide improved subtilase enzymes, which are suitable for removal of egg stains from for example laundry and/or hard surfaces.

SUMMARY OF THE INVENTION

Thus, in a first aspect the present invention relates to a subtilase enzyme having improved wash performance on egg stains, the subtilase being selected from the group consisting of
  (a) a subtilase having an amino acid sequence which has more than 99.26% identity with the amino acid sequence shown as amino acids I to 269 of SEQ ID NO:2; and
  (b) a subtilase encoded by the subtilase encoding part of the polynucleotide cloned into a plasmid fragment present in *Escherichia coli* MT173 DSM 15575, or a variant thereof having at least 99.26% identity to said subtilase; and
  (c) a subtilase having an amino acid sequence which has more than 97.40% identity with the amino acid sequence shown as amino acids 1 to 269 of SEQ ID NO:4; and
  (d) a subtilase encoded by the subtilase encoding part of the polynucleotide cloned into a plasmid fragment present in *Escherichia coli* MT173 DSM 15574, or a variant thereof having at least 97.40% identity to said subtilase.

In a second aspect the present invention relates to an isolated polynucleotide comprising a nucleic acid sequence that encodes for the subtilases according to the invention.

In a third aspect the present invention relates to an isolated polynucleotide encoding a subtilase, selected from the group consisting of
  (a) a polynucleotide having at least 88% identity with the nucleic acid sequence shown as nucleotides 1 to 807 SEQ ID NO:1; and
  (b) the subtilase encoding part of the polynucleotide that has been cloned into a plasmid present in *Escherichia coli* MT173 DSM 15575, or a variant thereof having at least 88% identity to said nucleic acid sequence.
  (c) a polynucleotide having at least 88% identity with the nucleic acid sequence shown as nucleotides 1 to 807 SEQ ID NO:3; and
  (d) the subtilase encoding part of the polynucleotide that has been cloned into a plasmid present in *Escherichia coli* MT173 DSM 15574, or a variant thereof having at least 88% identity to said nucleic acid sequence.

In a fourth aspect the present invention relates to a nucleic acid construct comprising the nucleic acid sequence according to the invention operably linked to one or more control sequences capable of directing the expression of the subtilase in a suitable host.

In a fifth aspect the present invention relates to a recombinant expression vector comprising the nucleic acid construct according to the invention, a promoter, and transcriptional and translational stop signals.

In a sixth aspect the present invention relates to a recombinant host cell comprising the nucleic acid construct of the invention.

In a seventh aspect the present invention relates to a method for producing the subtilase according to the invention, the method comprising:
(a) cultivating a recombinant host cell according to the invention under conditions conducive to the production of the subtilase; and
(b) recovering the subtilase.

In an eight aspect the present invention relates to a cleaning or detergent composition, preferably a laundry or dish wash composition, comprising the subtilase according to the invention.

Further aspects of the present invention relate to use of the subtilases according to the invention in a cleaning or detergent composition; use of the subtilases or the compositions according to the invention for removal of egg stains; a method for cleaning or washing, including a method for removal of egg stains from a hard surface or laundry comprising contacting the hard surface or the laundry with the composition of the invention.

Concerning alignment and numbering reference is made to FIG. 1 which shows alignments between subtilisin BPN' (a) (BASBPN) and the novel subtilases of the invention (b) and (c).

These alignments are in this patent application used as a reference for numbering the residues.

DEFINITIONS

Prior to discussing this invention in further detail, the following terms and conventions will first be defined.

| NOMENCLATURE OF AMINO ACIDS | | |
|---|---|---|
| A = | Ala = | Alanine |
| V = | Val = | Valine |
| L = | Leu = | Leucine |
| I = | Ile = | Isoleucine |
| P = | Pro = | Proline |
| F = | Phe = | Phenylalanine |
| W = | Trp = | Tryptophan |
| M = | Met = | Methionine |
| G = | Gly = | Glycine |
| S = | Ser = | Serine |
| T = | Thr = | Threonine |
| C = | Cys = | Cysteine |
| Y = | Tyr = | Tyrosine |
| N = | Asn = | Asparagine |
| Q = | Gln = | Glutamine |
| D = | Asp = | Aspartic Acid |
| E = | Glu = | Glutamic Acid |
| K = | Lys = | Lysine |
| R = | Arg = | Arginine |
| H = | His = | Histidine |
| X = | Xaa = | Any amino acid |

| NOMENCLATURE OF NUCLEIC ACIDS | |
|---|---|
| A = | Adenine |
| G = | Guanine |
| C = | Cytosine |
| T = | Thymine (only in DNA) |
| U = | Uracil (only in RNA) |

NOMENCLATURE AND CONVENTIONS FOR DESIGNATION OF VARIANTS

In describing the various subtilase enzyme variants produced or contemplated according to the invention, the following nomenclatures and conventions have been adapted for ease of reference:

A frame of reference is first defined by aligning the isolated or parent enzyme with subtilisin BPN' (BASBPN).

"Homology" or "homologous to" is in the context of the present invention to be understood in its conventional meaning and the "homology" between two amino acid sequences should be determined by use of the "Similarity" defined by the GAP program from the University of Wisconsin Genetics Computer Group (GCG) package using default settings for alignment parameters, comparison matrix, gap and gap extension penalties. Default values for GAP penalties, i.e. GAP creation penalty of 3.0 and GAP extension penalty of 0.1 (Program Manual for the Wisconsin Package, Version 8, August 1994, Genetics Computer Group, 575 Science Drive, Madison, Wis., USA 53711). The method is also described in S. B. Needleman and C. D. Wunsch, Journal of Molecular Biology, 48, 443-445 (1970). Identities can be extracted from the same calculation. The homology between two amino acid sequences can also be determined by "identity" or "similarity" using the GAP routine of the GCG package version 9.1 with default setting for alignment parameters, comparison matrix, gap and gap extension penalties can also be applied using the following parameters: gap creation penalty =8 and gap extension penalty =8 and all other parameters kept at their default values. The output from the routine is besides the amino acid alignment the calculation of the "Percent Identity" and the "Similarity" between the two sequences. The numbers calculated using GCG package version 9.1 is slightly different from the version 8.

Another method is to use known recognized alignments between subtilases, such as the alignment indicated in WO 91/00345. In most cases the differences will not be of any importance.

Such an alignment between subtilisin BPN' (BASBPN) and the novel subtilases of the invention is indicated in FIG. 1.

Thereby, a number of deletions and insertions will be defined in relation to BASBPN. In FIG. 1, the novel subtilases according to the invention have 6 deletions in positions 36, 58, 158, 162, 163, and 164 in comparison to BASBPN. These deletions are in FIG. 1 indicated by asterixes (*).

The various modifications performed in a parent enzyme are indicated in general using three elements as follows:

Original Amino Acid Position Substituted Amino Acid

The notation G195E means a substitution of a glycine in position 195 with a glutamic acid.

Position Substituted Amino Acid

In the case where the original amino acid residue may be any amino acid residue, a short hand notation may at times be used indicating only the position and substituted amino acid: 170Ser or 170S.

Such a notation is particular relevant in connection with modification(s) in homologous subtilases (vide infra).

Original Amino Acid Position

Such a notation is in particular relevant when the identity of the substituting amino acid residue(s) is immaterial. The substitution of any amino acid residue acid for glycine in position 195 is designated as: Gly195 or G195.

Position

When both the original amino acid(s) and substituted amino acid(s) may comprise any amino acid, then only the position is indicated, e.g.: 170.

Original Amino Acid Position {Substituted Amino Acid1, ..., Substituted Amino Acidn}

When the original amino acid(s) and/or substituted amino acid(s) may comprise more than one, but not all amino acid(s), then the selected amino acids are indicated inside brackets: { }.

For specific variants the specific three or one letter codes are used, including the codes Xaa and X to indicate any amino acid residue.

Substitutions:

the substitution of Glutamic acid for glycine in position 195 is designated as:

Gly195Glu or G195E or the substitution of any amino acid residue acid for glycine in position 195 is designated as:

Gly195Xaa or G195X or

Gly195 or G195

The substitution of serine for any amino acid residue in position 170 would thus be designated:

Xaa170Ser or X170S.

or

170Ser or 170S

Such a notation is particular relevant in connection with modification(s) in homologous subtilases (vide infra). 170Ser is thus meant to comprise e.g. both a Lys170Ser modification in BASBPN and Arg170Ser modification in the subtilase according to the invention (cf. FIG. 1).

For a modification where the original amino acid(s) and/or substituted amino acid(s) may comprise more than one, but not all amino acid(s), the substitution of glycine, alanine, serine or threonine for arginine in position 170 would be indicated by:

Arg170{Gly,Ala,Ser,Thr} or R170{G,A,S,T} to indicate the variants

R170G, R170A, R170S, and R170T.

Deletions

A deletion of glycine in position 195 will be indicated by:

Gly195* or G195*

Correspondingly, the deletion of more than one amino acid residue, such as the deletion of glycine and leucine in positions 195 and 196 will be designated:

Gly195*+Leu196* or G195*+L196*

Insertions

The insertion of an additional amino acid residue such as e.g. a lysine after G195 is indicated by:

Gly195GlyLys or G195GK;

or when more than one amino acid residue is inserted, such as e.g. a Lys, and Ala after G195 this will be indicated as:

Gly195GlyLysAla or G195GKA

In such cases, the inserted amino acid residue(s) are numbered by the addition of lower case letters to the position number of the amino acid residue preceding the inserted amino acid residue(s). In the above example, the sequences 194 to 196 would thus be:

```
              194 195 196
    BLSAVI    A - G - L 194 195 195a 195b 196
    Variant   A - G - K  - A  - L
```

In cases where an amino acid residue identical to the existing amino acid residue is inserted it is clear that degeneracy in the nomenclature arises. If for example a glycine is inserted after the glycine in the above example this would be indicated by G195GG. The same actual change could just as well be indicated as A194AG for the change from

```
              194 195 196
    BLSAVI    A - G - L
    to 194 195  195a 196
    Variant   A - G  - G  - L
              194 194a 195  196
```

Such instances will be apparent to the skilled person, and the indication G195GG and corresponding indications for this type of insertions are thus meant to comprise such equivalent degenerate indications.

Filling a Gap:

Where a deletion in an enzyme exists in the reference comparison with the subtilisin BPN' sequence used for the numbering, an insertion in such a position is indicated as:

*36Asp or *36D for the insertion of an aspartic acid in position 36

Multiple Modifications:

Variants comprising multiple modifications are separated by pluses, e.g.:

Arg170Tyr+Gly195Glu or R170Y+G195E representing modifications in positions 170 and 195 substituting tyrosine and glutamic acid for arginine and glycine, respectively.

Thus, Tyr167{Gly,Ala,Ser,Thr}+Arg170{Gly,Ala,Ser,Thr} designates the following variants:

| | |
|---|---|
| Tyr167Gly + Arg170Gly, | Tyr167Gly + Arg170Ala, |
| Tyr167Gly + Arg170Ser, | Tyr167Gly + Arg170Thr, |
| Tyr167Ala + Arg170Gly, | Tyr167Ala + Arg170Ala, |
| Tyr167Ala + Arg170Ser, | Tyr167Ala + Arg170Thr, |
| Tyr167Ser + Arg170Gly, | Tyr167Ser + Arg170Ala, |
| Tyr167Ser + Arg170Ser, | Tyr167Ser + Arg170Thr, |
| Tyr167Thr + Arg170Gly, | Tyr167Thr + Arg170Ala, |
| Tyr167Thr + Arg170Ser, and | Tyr167Thr + Arg170Thr. |

This nomenclature is particular relevant relating to modifications aimed at substituting, replacing, inserting or deleting amino acid residues having specific common properties, such as residues of positive charge (K, R, H), negative charge (D, E), or conservative amino acid modification(s) of e.g. Tyr167{Gly,Ala,Ser,Thr}+Arg170{Gly,Ala,Ser,Thr}, which signifies substituting a small amino acid for another small amino acid. See the section "Detailed description of the invention" for further details.

Proteases

Enzymes cleaving the amide linkages in protein substrates are classified as proteases, or (interchangeably) peptidases (see Walsh, 1979, *Enzymatic Reaction Mechanisms*. W.H. Freeman and Company, San Francisco, Chapter 3).

Numbering of Amino Acid Positions/Residues

If nothing else is mentioned, the amino acid numbering used herein corresponds to that of the subtilase BPN' (BASBPN) sequence. For further description of the BPN' sequence, see FIG. 1 or Siezen et al., *Protein Engng.* 4 (1991) 719-737.

Serine Proteases

A serine protease is an enzyme which catalyzes the hydrolysis of peptide bonds, and in which there is an essential serine residue at the active site (White, Handler and Smith, 1973 *"Principles of Biochemistry,"* Fifth Edition, McGraw-Hill Book Company, NY, pp. 271-272).

The bacterial serine proteases have molecular weights in the 20,000 to 45,000 Dalton range. They are inhibited by diisopropyl fluorophosphate. They hydrolyze simple terminal esters and are similar in activity to eukaryotic chymotrypsin, also a serine protease. A more narrow term, alkaline protease, covering a sub-group, reflects the high pH optimum of some of the serine proteases, from pH 9.0 to 11.0 (for review, see Priest (1977) *Bacteriological Rev.* 41 711-753).

Subtilases

Siezen et al have proposed a sub-group of the serine proteases tentatively designated subtilases, Protein Engng, 4 (1991) 719-737 and Siezen et al. *Protein Science* 6 (1997) 501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of the subtilases. A wide variety of subtilases have been identified, and the amino acid sequence of a number of subtilases has been determined. For a more detailed description of such subtilases and their amino acid sequences reference is made to Siezen et al. (1997).

One subgroup of the subtilases, I-S1 or "true" subtilisins, comprises the "classical" subtilisins, such as subtilisin 168 (BSS168), subtilisin BPN' (BASBPN), subtilisin Carlsberg (BLSCAR)(ALCALASE®, NOVOZYMES A/S), and subtilisin DY (BSSDY).

A further subgroup of the subtilases, I-S2 or high alkaline subtilisins, is recognized by Siezen et al. (supra). Subgroup I-S2 proteases are described as highly alkaline subtilisins and comprises enzymes such as subtilisin PB92 (BAALKP) (MAXACAL@, Gist-Brocades NV), subtilisin 309 (BLSAVI)(SAVINASE®, NOVOZYMES A/S), subtilisin 147 (BLS147) (ESPERASE®, NOVOZYMES A/S), and alkaline elastase YaB (BSEYAB).

Parent Subtilase

The term "parent subtilase" describes a subtilase defined according to Siezen et al. (1991 and 1997). For further details, see description of "SUBTILASES" immediately above. A parent subtilase may also be a subtilase isolated from a natural source, wherein subsequent modifications have been made while retaining the characteristic of a subtilase. Furthermore, a parent subtilase may also be a subtilase which has been prepared by the DNA shuffling technique, such as described by J. E. Ness et al., Nature Biotechnology, 17, 893-896 (1999).

Alternatively the term "parent subtilase" may be termed "wild type subtilase".

Modification(s) of a Subtilase

The term "modification(s)" used herein is defined to include chemical modification of a subtilase as well as genetic manipulation of the DNA encoding a subtilase. The modification(s) can be replacement(s) of the amino acid side chain(s), substitution(s), deletion(s) and/or insertions in or at the amino acid(s) of interest.

Subtilase Variant

In the context of this invention, the term subtilase variant or mutated subtilase means a subtilase that has been produced by an organism which is expressing a mutant gene derived from a parent micro organism which possessed an original or parent gene and which produced a corresponding parent enzyme, the parent gene having been mutated in order to produce the mutant gene from which said mutated subtilase protease is produced when expressed in a suitable host. Analogously, the mutant gene may also be derived from a parent gene produced by DNA shuffling technique.

Homologous Subtilase Sequences

In the present context, the homology between two amino acid sequences is described by the parameter "identity".

In order to determine the degree of identity between two subtilases, the GAP routine of the GCG package version 9.1 can be applied (infra) using the same settings. The output from the routine is besides the amino acid alignment the calculation of the "Percent Identity" between the two sequences.

Based on this description it is routine for a person skilled in the art to identify suitable homologous subtilases and corresponding homologous active site loop regions, which can be modified according to the invention.

Isolated Polynucleotide

The term "isolated polynucleotide" as used herein refers to a polynucleotide, which has been isolated and purified and is thus in a form suitable for use within genetically engineered protein production systems. Such isolated molecules may be those that are separated from their natural environment and include cDNA and genomic clones as well as polynucleotides derived from DNA shuffling experiments or from site-directed autogenesis experiments. Isolated polynucleotides of the present invention are free of other genes with which they are ordinarily associated, but may include 5' and 3' untranslated regions such as promoters and terminators. The identification of associated regions will be evident to one of ordinary skill in the art (see for example Dynan and Tijan, *Nature* 316:774-78, 1985). The term "isolated nucleic acid sequence" may alternatively be termed "isolated DNA sequence", "cloned nucleic acid sequence" or "cloned DNA sequence".

Isolated Protein

When applied to a protein, the term "isolated" indicates that the protein has been removed from its native environment.

In a preferred form, the isolated protein is substantially free of other proteins, particularly other homologous proteins (i.e. "homologous impurities" (see below)).

An isolated protein is more than 10% pure, preferably more than 20% pure, more preferably more than 30% pure, as determined by SDS-PAGE. Further, it is preferred to provide the protein in a highly purified form, i.e. more than 40% pure, more than 60% pure, more than 80% pure, more preferably more than 95% pure, and most preferably more than 99% pure, as determined by SDS-PAGE.

The term "isolated protein" may alternatively be termed "purified protein".

Homologous Impurities

The term "homologous impurities" means any impurity (e.g. another polypeptide than the subtilase of the invention), which originate from the homologous cell where the subtilase of the invention is originally obtained from.

Obtained From

The term "obtained from" as used herein in connection with a specific microbial source means that the polynucleotide and/or subtilase produced by the specific source, or by a cell in which a gene from the source has been inserted.

Substrate

The term "substrate" used in connection with a substrate for a protease should be interpreted in its broadest form as comprising a compound containing at least one peptide bond susceptible to hydrolysis by a subtilisin protease.

Product

The term "product" used in connection with a product derived from a protease enzymatic reaction should in the context of the present invention be interpreted to include the products of a hydrolysis reaction involving a subtilase protease. A product may be the substrate in a subsequent hydrolysis reaction.

Wash Performance

In the present context, the term "wash performance" is used as an enzyme's ability to remove soil, in particular egg stains present on the object to the cleaned during e.g. wash or hard surface cleaning. See also the "Model Detergent Wash Performance Test" in Example 2.

% Removed Protein Film

In the present context, the term "% Removed Protein Film" is used as an enzyme's ability to remove soil, in particular egg stains present on the object to the cleaned during automatic dish wash. Performance data originate from gravimetric measurements of the steel plates as clean, soiled and washed. The performance is calculated as:

$$\% \text{ Removed Protein Film } (\% RPF) = \frac{(Weight_{soiled} - Weight_{washed}) \times 100}{Weight_{soiled} - Weight_{clean}}$$

The data are fitted to the four-parameter logistic model that can be written as:

$$F(z) = Y_0 + V_{max} * C^\lambda / (k_s^\lambda + C^\lambda)$$

Where F(z) is the response calculated from $Y_0$ as the intercept, $Y_0 + V_{max}$ being maximum response, C the enzyme dosage and $k_s$ being the half-saturation value. $\lambda$ is the steepness parameter that in a Michaelis-Menten model is equal 1, but here it is equal or different from one as we are allowing S-shaped curves to be fitted. Each curve fit is compared to the performance of the reference enzyme.

For further details, see the "Mini scale Automatic Dish Washing (ADW mini wash)" in Example 4, herein.

BRIEF DESCRIPTION OF THE DRAWINGS

FIG. 1 shows an alignment between subtilisin BPN' (a) and the amino acid sequence of the novel subtilases of the invention (b) and (c) using the GAP routine mentioned above.

FIG. 2 schematically depicts the set up of the ADW mini wash as described in example 4.

FIG. 3 shows the results of the ADW mini wash test method on egg yolk soil.

FIG. 4 shows the results of the AMSA test method (example 5) in combination with a commercially available.

DETAILED DESCRIPTION OF THE INVENTION

In a first interesting aspect of the present invention, the subtilase enzyme having improved wash performance on egg stains is an isolated subtilase which has more than 99.26% identity with the amino acid sequence shown as amino acids 1 to 269 of SEQ ID NO:2 (i.e. the mature subtilase). In an interesting embodiment of the invention, the subtilase has more than 99.26% or more than 99.63% identity with the amino acid sequence shown as amino acids 1 to 269 of SEQ ID NO:2 (hereinafter "homologous subtilases"). In another interesting embodiment of the invention, the isolated subtilase consists of the amino acid sequence shown as amino acids 1 to 269 of SEQ ID NO:2.

In a further interesting aspect of the present invention, the subtilase enzyme having improved wash performance on egg stains is an isolated subtilase which has more than 97.40% identity with the amino acid sequence shown as amino acids 1 to 269 of SEQ ID NO:4 (i.e. the mature subtilase). In an interesting embodiment of the invention, the subtilase has more than 97.40%, or more than 97.77%, or more than 98.14%, or more than 98.51%, or more than 98.89%, or more than 99.26%, or more than 99.63% identity with the amino acid sequence shown as amino acids 1 to 269 of SEQ ID NO:4 (hereinafter "homologous subtilases"). In another interesting embodiment of the invention, the isolated subtilase consists of the amino acid sequence shown' as amino acids 1 to 269 of SEQ ID NO:4.

Alignments of sequences and calculation of identity scores can be done using a full Smith-Waterman alignment, useful for both protein and DNA alignments. The default scoring matrices BLOSUM50 and the identity matrix are used for protein and DNA alignments respectively. The penalty for the first residue in a gap is −12 for proteins and −16 for DNA, while the penalty for additional residues in a gap is −2 for proteins and −4 for DNA. Align is from the Fasta package version v3.1t11 (W. R. Pearson and D. J. Lipman (1988), "Improved Tools for Biological Sequence Analysis", PNAS 85:2444-2448, and W. R. Pearson (1990) "Rapid and Sensitive Sequence Comparison with FASTP and FASTA" Methods in Enzymology 183:63-98).

By performing such alignments, the following identities (in percentage) between the amino acid sequences of the subtilase having the amino acid sequence of SEQ ID NO:2 and SEQ ID NO:4, and various known subtilases were found:

| | BLSavi | BLAP | BASBPN | BLSCAR | SEQ ID NO: 6 | WO 01/75087 SEQ ID NO: 16 | WO 01/75087 SEQ ID NO: 24 |
|---|---|---|---|---|---|---|---|
| BLSavi | 100 | | | | | | |
| BLAP | | 100 | | | | | |
| BASBPN | | | 100 | | | | |
| BLSCAR | | | | 100 | | | |

-continued

| | BLSavi | BLAP | BASBPN | BLSCAR | SEQ ID NO: 6 | WO 01/75087 SEQ ID NO: 16 | WO 01/75087 SEQ ID NO: 24 |
|---|---|---|---|---|---|---|---|
| SEQ ID NO: 6 | | | | | 100 | | |
| WO 01/75087 SEQ ID NO: 16 | 88.1 | 87.36 | 60.00 | 55.84 | 97.03 | 100 | |
| WO 01/75087 SEQ ID NO: 24 | 91.08 | 90.34 | 59.64 | 57.66 | 95.54 | | 100 |
| SEQ ID NO: 4 | 91.5 | 90.7 | 60.7 | 59.1 | 95.91 | 96.65 | 97.40 |
| SEQ ID NO: 2 | 88.1 | 87.4 | 59.3 | 55.8 | 96.28 | 99.26 | 95.17 |

[1])BLAP (*Bacillus lentus* Alkaline Protease) has been described in U.S. Pat. No. 5,352,604

It is well-known in the art that a so-called conservative substitution of one amino acid residue to a similar amino acid residue is expected to produce only a minor change in the characteristic of the enzyme.

Table I below lists groups of conservative amino acid substitutions.

TABLE I

| Conservative amino acid substitutions Common Property | Amino Acid |
|---|---|
| Basic (positive charge) | R = arginine |
| | K = lysine |
| | H = histidine |
| Acidic (negative charge) | E = glutamic acid |
| | D = aspartic acid |
| Polar | Q = glutamine |
| | N = asparagine |
| Hydrophobic | L = leucine |
| | I = isoleucine |
| | V = valine |
| | M = methionines |
| Aromatic | F = phenylalanine |
| | W = tryptophane |
| | Y = tyrosine |
| Small | G = glycine |
| | A = alanine |
| | S = serine |
| | T = threonine |

Therefore, in a further interesting embodiment of the invention, the subtilase having the amino acid sequence of SEQ ID NO:2 and SEQ ID NO:4 is combined with a substitution, deletion and/or insertion of one or more amino acid residues.

Especially, combinations with other modifications known in the art to provide improved properties to the enzyme are envisaged. The art describes a number of subtilase variants with different improved properties and a number of those is mentioned in the "Background of the invention" section herein (vide supra).

Such combinations comprise the positions: 222 (improves oxidation stability), 218 (improves thermal stability), substitutions in the $Ca^{2+}$-binding sites stabilizing the enzyme, e.g. position 76, and many other apparent from the prior art.

In further embodiments, a subtilase variant described herein may advantageously be combined with one or more modification(s) in any of the positions:

27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274 (BPN' numbering).

Specifically, the following BLSAVI, BLSUBL, BSKSMK, and BAALKP modifications are considered appropriate for combination:

K27R, *36D, S56P, N76D, S87N, G97N, S101G, S103A, V104A, V104I, V104N, V104Y, H120D, N123S, G159D, Y167, R170, Q206E, N218S, M222S, M222A, T224S, A232V, K235L, Q236H, Q245R, N248D, N252K and T274A.

Furthermore, variants comprising any of the modifications S101G+V104N, S87N+S101G+V104N, K27R+V104Y+N123S+T274A, N76D+S103A+V104I or N76D+V104A, or other combinations of the modifications K27R, N76D, S101G, S103A, V104N, V104Y, V104I, V104A, N123S, G159D, A232V, Q236H, Q245R, N248D, N252K, T274A in combination with any one or more of the modification(s) mentioned above exhibit improved properties.

A particular interesting variant is a variant, which in addition to modifications according to the invention contains the following substitutions:

S101G+S103A+V104I+G159D+A232V+Q236H+Q245R+N248D+N252K.

Moreover, subtilase variants of the main aspect(s) of the invention are preferably combined with one or more modification(s) in any of the positions 129, 131 and 194, preferably as 129K, 131H and 194P modifications, and most preferably as P129K, P131H and A194P modifications. Any of those modification(s) are expected to provide a higher expression level of the subtilase variant in the production thereof.

Furthermore, it is contemplated that insertion of at least one additional amino acid residue in the active site (b) loop region, corresponding to insertion of at least one additional amino acid residue from position 95 to position 103 (BASBPN numbering), will confer additional wash performance to the subtilase of the invention. In particular, it is preferred to insert at least one additional amino acid residue, such as one additional amino acid residue, in the following positions: between positions 98 and 99, and between positions 99 and 100.

Moreover, isolated subtilases, preferably in a purified form, having immunochemical identity or partial immunochemical identity to the subtilase having the amino acid sequence of SEQ ID NO:2 or SEQ ID NO:4 are also considered as being within the scope of the present invention. The immunochemical properties are determined by immunological cross-reaction identity tests by the well-known Ouchterlony double immunodiffusion procedure. Specifically, an antiserum containing polyclonal antibodies which are immunoreactive or bind to epitopes of the subtilase having the amino acid sequence of SEQ ID NO:2 or SEQ ID NO:4 are prepared by immunizing rabbits (or other rodents) according to the procedure described by Harboe and Ingild, In N. H. Axelsen, J. Kræll, and B. Weeks, editors, *A Manual of Quantitative Immunoelectrophoresis*, Blackwell Scientific Publications, 1973, Chapter 23, or Johnstone and Thorpe, *Immunochemistry in Practice*, Blackwell Scientific Publications, 1982 (more specifically pages 27-31). A subtilase having immunochemical identity is a subtilase, which reacts with the antiserum in an identical fashion such as total fusion of precipitates, identical precipitate morphology, and/or identical electrophoretic mobility using a specific immunochemical technique. Axelsen, Bock, and Krøll describe a further explanation of immunochemical identity in N. H. Axelsen, J. Krøll, and B. Weeks, editors, *A Manual of Quantitative Immunoelectrophoresis*, Blackwell Scientific Publications, 1973, Chapter 10. A subtilase having partial immunochemical identity is a subtilase, which reacts with the antiserum in a partially identical fashion such as partial fusion of precipitates, partially identical precipitate morphology, and/or partially identical electrophoretic mobility using a specific immunochemical technique. Bock and Axelsen describe partial immunochemical identity in N.H. Axelsen, J. Krøll, and B. Weeks, editors, *A Manual of Quantitative Immunoelectrophoresis*, Blackwell Scientific Publications, 1973, Chapter 11.

The antibody may also be a monoclonal antibody. Monoclonal antibodies may be prepared and used, e.g. according to the methods of E. Harlow and D. Lane, editors, 1988, *Antibodies, A Laboratory Manual*, Cold Spring Harbor Press, Cold Spring Harbor, N.Y.

The present inventors have isolated the gene encoding the subtilase having the amino acid sequence shown in SEQ ID NO:2 and inserted it into *E. coli* MT173. The *E. coli* MT173 strain harbouring the gene was deposited according to the Budapest Treaty on the International Recognition of the Deposits of Microorganisms for the Purpose of Patent Procedures on 8 Feb. 2000 at the Deutsche Sammlung von Mikroorganismen und Zellkultruren GmbH, Mascheroder Weg 1 B, D-38124 Braunschweig, Germany, and designated the accession No. DSM 15575.

The present inventors have isolated the gene encoding the subtilase having the amino acid sequence shown in SEQ ID NO:4 and inserted it into *E. coli* MT173. The *E. coli* MT173 strain harbouring the gene was deposited according to the Budapest Treaty on the International Recognition of the Deposits of Microorganisms for the Purpose of Patent Procedures on 8 Feb. 2000 at the Deutsche Sammlung von Mikroorganismen und Zellkulturen GmbH, Mascheroder Weg 1 B, D-38124 Braunschweig, Germany, and designated the accession No. DSM 15574.

In an interesting embodiment of the invention, the subtilase has more than 99.26% or more than 99.63% identity with the subtilase encoded by the subtilase encoding part of the polynucleotide cloned into a plasmid fragment present in *E. coli* MT173 deposited under the accession No. DSM 15575.

In another interesting embodiment of the invention, the subtilase has more than 97.40%, or more than 97.77%, or more than 98.14%, or more than 98.51%, or more than 98.89%, or more than 99.26%, or more than 99.63% identity with the subtilase encoded by the subtilase encoding part of the polynucleotide cloned into a plasmid fragment present in *E. coli* MT173 deposited under the accession No. DSM 15574.

As mentioned above, the subtilase of the invention exhibits excellent wash performance on egg stains. Therefore, in order to enable the skilled person—at an early stage of his development work—to select effective and preferred subtilases for this purpose, the present inventors have provided a number of suitable preliminary tests, which can easily be carried out by the skilled person in order to initially assess the performance of the subtilase in question.

Thus, the "Model Detergent Wash Performance Test" disclosed in Example 2, herein, may be employed to assess the efficiency of the selected subtilase. In other words, the "Model Detergent Wash Performance Test" may be employed to assess the ability of a subtilase, when incorporated in a standard detergent composition, to remove egg stains from a textile surface as compared to a reference system (incorporated in the same model detergent system and tested under identical conditions). Using this test, the suitability of a selected subtilase to remove egg stains can be initially investigated, the rationale being that if a selected subtilase does not show a significant improvement in the test compared to the reference enzyme, it is normally not necessary to carry out further test experiments.

Therefore, subtilases which are particular interesting for laundry wash purposes, are such subtilases which when tested in a model detergent composition comprising

| | |
|---|---|
| 6.2% | LAS (Nansa 80S) |
| 2% | Sodium salt of $C_{16}$-$C_{18}$ fatty acid |
| 4% | Non-ionic surfactant (Plurafax LF404) |
| 22% | Zeolite P |
| 10.5% | $Na_2CO_3$ |
| 4% | $Na_2Si_2O_5$ |
| 2% | Carboxymethylcellulose (CMC) |
| 6.8% | Acrylate liquid CP5 40% |
| 20% | Sodium perborate (empirical formula $NaBO_2.H_2O_2$) |
| 0.2% | EDTA |
| 21% | $Na_2SO_4$ |
| | Water (balance) | as described in the "Model Detergent Wash Performance Test" herein, shows an improved wash performance on egg stains as compared to a reference enzyme tested under identical conditions.

The improvement in the wash performance may be quantified by employing the so-called "Performance factor" defined in Example 2, herein.

In a very interesting embodiment of the invention, the subtilase of the invention, when tested in the "Wash Performance Test", has a Performance Factor of at least 1, such as at least 1.5, e.g. at least 2, preferably at least 2.5, such as at least 3, e.g. at least 3.5, in particular at least 4, such as at least 4.5, e.g. at least 5.

Evidently, it is preferred that the subtilase of the invention fulfils the above criteria on at least the stated lowest level, more preferably at the stated intermediate level and most preferably on the stated highest level. "

The full scale Automatic Dish Washing (ADW) test" disclosed in Example 3 or the "Mini scale Automatic Dish Washing (ADW mini wash)" disclosed in Example 4 or the "Automated Mechanical Stress Assay (AMSA)" disclosed in Example 5, all herein, may be employed to assess the efficiency of the selected subtilase in Automatic Dish Washing. In other words, the tests may be employed to assess the ability of a subtilase, when incorporated in a detergent composition (commercial or standard), to remove egg stains from a hard surface as compared to a reference system (incorporated in the same detergent system and tested under identical conditions). Using this test, the suitability of a selected subtilase to remove egg stains can be initially investigated, the rationale being that if a selected subtilase does not show a significant improvement in the test compared to the reference enzyme, it is normally not necessary to carry out further test experiments.

Therefore, subtilases which are particular interesting for automatic dish washing purposes are such subtilases which, when tested in a model detergent composition comprising:

| | |
|---|---|
| Sodium Tripolyphosphate | 23.0% |
| Sodium Citrate Dihydrate | 22.3% |
| Sodium Perborate Monohydrate | 6.0% |
| Tetraacetyl Ethylendiamine | 2.0% |
| Sodium Disilicate (noncrystaline) | 5.0% |
| Linear Fatty Alcohol Ethoxylate (non-ionic surfactant, low foaming) | 2.0% |
| Maleic acid/Acrylic acid copolymer (Sodium salt, 50% active on Sodium Carbonate) | 4.0% |
| Sodium Carbonate, anhydrous | add to 100% | as described in the tests in Examples 3, 4 or 5 herein, shows an improved performance on egg stains as compared to a reference enzyme tested under identical conditions.

The subtilase of the invention may be constructed by standard techniques for artificial creation of diversity, such as by DNA shuffling of different subtilase genes (see WO 95/22625 and J. E. Ness et al., Nature Biotechnology, 17, 893-896 (1999)).

Obviously, the subtilase of the invention may also be isolated from a natural source, i.e. the subtilase of the invention may, for example, be a bacterial subtilase, e.g. a gram positive bacterial subtilase such as a *Bacillus* polypeptide, e.g., a *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus megaterium, Bacillus stearothermophilus, Bacillus subtilis*, or *Bacillus thuringiensis* subtilase; or a Streptomyces subtilase, e.g., a *Streptomyces lividans* or *Streptomyces murinus* subtilase; or a gram negative bacterial subtilase, e.g., an *E. coli* or a *Pseudomonas* sp. subtilase.

The subtilase of the present invention may also be a fungal polypeptide, and more preferably a yeast subtilase such as a *Candida, Kluyveromyces, Pichia, Saccharomyces, Schizosaccharomyces*, or *Yarrowia* subtilase; or more preferably a filamentous fungal subtilase such as an *Acremonium, Aspergillus, Aureobasidium, Cryptococcus, Filibasidium, Fusarium, Humicola, Magnaporthe, Mucor, Myceliophthora, Neocallimastix, Neurospora, Paecilomyces, Penicillium, Piromyces, Schizophyllum, Talaromyces, Thermoascus, Thielavia, Tolypocladium*, or *Trichoderma* subtilase.

In an interesting embodiment, the subtilase is a *Saccharomyces carlsbergensis, Saccharomyces cerevisiae, Saccharomyces diastaticus, Saccharomyces douglasli, Saccharomyces kluyveri, Saccharomyces norbensis* or *Saccharomyces oviformis* subtilase.

In another interesting embodiment, the subtilase is an *Aspergillus aculeatus, Aspergillus awamori, Aspergillus foetidus, Aspergillus japonicus, Aspergillus nidulans, Aspergillus niger, Aspergillus oryzae, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Trichoderma harzianum, Trichoderma koningii, Trichoderma longibrachiatum, Trichoderma reesei*, or *Trichoderma viride* subtilase.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zelikulturen GmbH (DSM), Centraalbureau Voor Schimmelcultures (CBS), and Agricultural Research Service Patent Culture Collection, Northern Regional Research Center (NRRL).

Furthermore, such subtilases may be identified and obtained from other sources including microorganisms isolated from nature (e.g., soil, composts, water, etc.) using the above-mentioned probes. Techniques for isolating microorganisms from natural habitats are well known in the art. Similarly screening a genomic or cDNA library of another microorganism may then derive the polynucleotide. Once a polynucleotide encoding a subtilase has been detected with the probe(s), the sequence may be isolated or cloned by utilizing techniques which are known to those of ordinary skill in the art (see, e.g., Sambrook et al, 1989, supra).

Many methods for cloning a subtilase of the invention and for introducing insertions into genes (e.g. subtilase genes) are well-known in the art, cf. the references cited in the "BACKGROUND OF THE INVENTION" section.

In general standard procedures for cloning of genes and introducing insertions (random and/or site directed) into said genes may be used in order to obtain a subtilase enzyme of the invention. For further description of suitable techniques reference is made to Examples herein (vide infra) and (Sambrook et al. (1989) Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 1995; Harwood, C. R., and Cutting, S. M. (eds.) "Molecular Biological Methods for *Bacillus*". John Wiley and Sons, 1990); and WO 96/34946.

Further, a subtilase enzyme of the invention may be constructed by standard techniques for artificial creation of diversity, such as by DNA shuffling of different subtilase genes (WO 95/22625; Stemmer WPC, Nature 370:389-91 (1994)). DNA shuffling of e.g. the gene encoding Savinase® with one or more partial subtilase sequences identified in nature will, after subsequent screening for improved wash performance, provide subtilases according to the invention.

Polynucleotides

The present invention also relates to an isolated polynucleotide, which encodes a subtilase of the present invention.

In one interesting embodiment, the polynucleotide has at least 88%, or at least 89%, at least 90%, at least 91%, at least 92%, at least 93%, at least 94%, at least 95%, at least 96%, at least 97%, at least 98%, or at least 99% identity with the polynucleotide shown as nucleotides 1 to 807 of SEQ ID NO:1; or at least 88%, or at least 89%, at least 90%, at least 91%, at least 92%, at least 93%, at least 94%, at least 95%, at least 96%, at least 97%, at least 98%, or at least 99% identity with the polynucleotide shown as nucleotides 1 to 807 of SEQ ID NO:3. In another interesting embodiment of the invention, the polynucleotide comprises the polynucleotide shown as nucleotides 1 to 807 of SEQ ID NO:1 or of SEQ ID NO:3, an allelic variant thereof, or a fragment thereof capable of encoding subtilases according to the invention. Obviously, the polynucleotide may consist of the polynucleotide shown as nucleotides 1 to 807 of SEQ ID NO:1 or SEQ ID NO:3.

The present invention also encompasses polynucleotides that encode a polypeptide having the amino acid sequence of SEQ ID NO:2, which differ from SEQ ID NO:2 by virtue of the degeneracy of the genetic code; the present invention further encompasses polynucleotides that encode a polypeptide having the amino acid sequence of SEQ ID NO:4, which differ from SEQ ID NO:4 by virtue of the degeneracy of the genetic code. The present invention also relates to subsequences of SEQ ID NO:1 that encode fragments of SEQ ID NO:2 that have proteolytic activity, and to subsequences of. SEQ ID NO:3 that encode fragments of SEQ ID NO:4 that have proteolytic activity.

A subsequence of SEQ ID NO:1 is a polynucleotide encompassed by nucleotides 1 to 807 SEQ ID NO:1 except that one or more nucleotides from the 5' and/or 3' end have been deleted; a subsequence of SEQ ID NO:3 is a polynucleotide encompassed by nucleotides 1 to 807 SEQ ID NO:3 except that one or more nucleotides from the 5' and/or 3' end have been deleted.

The techniques used to isolate or clone a polynucleotide encoding a polypeptide are known in the art and include isolation from genomic DNA, preparation from cDNA, or a combination thereof. The cloning of the polynucleotides of the present invention from such genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used.

An isolated polynucleotide can for example be obtained by standard cloning procedures used in genetic engineering to relocate the polynucleotide from its natural location to a different site where it will be reproduced. The cloning procedures may involve excision and isolation of a desired nucleic acid fragment comprising the polynucleotide encoding the subtilase, insertion of the fragment into a vector molecule, and incorporation of the recombinant vector into a host cell where multiple copies or clones of the polynucleotide will be replicated. The polynucleotide may be of genomic, cDNA, RNA, semi-synthetic, synthetic origin, or any combinations thereof.

For purposes of the present invention, the degree of identity between two polynucleotides is determined is described above.

Modification of a polynucleotide encoding a subtilase of the present invention may be necessary for the synthesis of subtilases substantially similar to the subtilase. The term "substantially similar" to the subtilase refers to non-naturally occurring forms of the subtilase. These subtilases may differ in some engineered way from the subtilase isolated from its native source, e.g., variants that differ in specific activity, thermostability, pH optimum, or the like. The variant sequence may be constructed on the basis of the polynucleotide presented as the polypeptide encoding part of SEQ ID NO:1, or on the basis of the polynucleotide presented as the polypeptide encoding part of SEQ ID NO:3, e.g., a subsequence thereof, and/or by introduction of nucleotide substitutions which do not give rise to another amino acid sequence of the subtilase encoded by the nucleic acid sequence, but which correspond to the codon usage of the host organism intended for production of the enzyme, or by introduction of nucleotide substitutions which may give rise to a different amino acid sequence. For a general description of nucleotide substitution see, e.g., Ford et al., 1991, *Protein Expression and Purifcation* 2: 95-107.

It will be apparent to those skilled in the art that such substitutions-can be made outside the regions critical to the function of the molecule and still result in an active subtilase. Amino acid residues essential to the activity of the polypeptide encoded by the isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for proteolytic activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Nucleic Acid Constructs

The present invention also relates to nucleic acid constructs comprising a polynucleotide of the present invention operably linked to one or more control sequences capable of directing the expression of the polypeptide in a suitable host cell.

An isolated polynucleotide encoding a subtilase of the present invention may be manipulated in a variety of ways to provide for expression of the subtilase. Manipulation of the polynucleotide prior to its insertion into a vector may be desirable or necessary depending on the expression vector. The techniques for modifying polynucleotides utilizing recombinant DNA methods are well-known in the art.

The control sequences include all components that are necessary or advantageous for the expression of a subtilase of the present invention. Each control sequence may be native or foreign to the polynucleotide encoding the subtilase. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a subtilase.

The control sequence may be an appropriate promoter sequence, a polynucleotide that is recognized by a host cell for expression of the nucleic acid sequence. The promoter sequence contains transcriptional control sequences that mediate the expression of the subtilase. The promoter may be any polynucleotide that shows transcriptional activity in the host cell of choice including mutant, truncated, and hybrid promoters, and may be obtained from genes encoding extracellular or intracellular subtilases either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the polynucleotide encoding the subtilase. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Romanos et al., 1992, supra, describe other useful terminators for yeast host cells.

The control sequence may also be a suitable leader sequence, a non-translated region of an mRNA that is important for translation by the host cell. The leader sequence is operably linked to the 5' terminus of the polynucleotide encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the polynucleotide and which, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding region that codes for an amino acid sequence linked to the amino terminus of a subtilase and directs the encoded subtilase into the cell's secretory pathway. The 5' end of the coding sequence of the polynucleotide may inherently contain a signal peptide coding region naturally linked in translation reading frame with the segment of the coding region that encodes the secreted subtilase. Alternatively, the 5' end of the coding sequence may contain a signal peptide coding region that is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the subtilase. However, any signal peptide coding region that directs the expressed subtilase into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Romanos et al., 1992, supra, describe other useful signal peptide coding regions.

The control sequence may also be a propeptide coding region that codes for an amino acid sequence positioned at the amino terminus of a subtilase. The resultant polypeptide is known as a proenzyme or propolypeptide (or a zymogen in some cases). A propolypeptide is generally inactive and can be converted to a mature active polypeptide by catalytic or autocatalytic is cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a subtilase, the propeptide region is positioned next to the amino terminus of a subtilase and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to a recombinant expression vector comprising the nucleic acid construct of the invention, a promoter, and transcriptional and translational stop signals.

The recombinant expression vector comprising the nucleic acid construct encoding the enzyme of the invention may be any vector that may conveniently be subjected to recombinant DNA procedures.

The choice of vector will often depend on the host cell into which it is to be introduced. Thus, the vector may be an autonomously replicating vector, i.e. a vector that exists as an extrachromosomal entity, the replication of which is independent of chromosomal replication, e.g. a plasmid. Alternatively, the vector may be one that on introduction into a host cell is integrated into the host cell genome in part or in its entirety and replicated together with the chromosome(s) into which it has been integrated.

The vector is preferably an expression vector in which the DNA sequence encoding the enzyme of the invention is operably linked to additional segments required for transcription of the DNA. In general, the expression vector is derived from plasmid or viral DNA, or may contain elements of both. The term "operably linked" indicates that the segments are arranged so that they function in concert for their intended purposes, e.g. transcription initiates in a promoter and proceeds through the DNA sequence coding for the enzyme.

The promoter may be any DNA sequence that shows transcriptional activity in the host cell of choice and may be derived from genes encoding proteins either homologous or heterologous to the host cell.

Examples of suitable promoters for use in bacterial host cells include the promoter of the *Bacillus stearothermophilus* maltogenic amylase gene, the *Bacillus licheniformis* alpha-amylase gene, the *Bacillus amyloliquefaciens* alpha-amylase gene, the *Bacillus subtilis* alkaline protease gene, or the *Bacillus pumilus* xylosidase gene, or the phage Lambda $P_R$ or $P_L$ promoters or the *E. coli* lac, trp or tac promoters.

The DNA sequence encoding the enzyme of the invention may also, if necessary, be operably connected to a suitable terminator.

The recombinant vector of the invention may further comprise a DNA sequence enabling the vector to replicate in the host cell in question.

The vector may also comprise a selectable marker, e.g. a gene the product of which complements a defect in the host cell, or a gene encoding resistance to e.g. antibiotics like kanamycin, chloramphenicol, erythromycin, tetracycline, spectinomycine, or the like, or resistance to heavy metals or herbicides.

To direct an enzyme of the present invention into the secretory pathway of the host cells, a secretory signal sequence (also known as a leader sequence, prepro sequence or pre sequence) may be provided in the recombinant vector. The secretory signal sequence is joined to the DNA sequence encoding the enzyme in the correct reading frame. Secretory signal sequences are commonly positioned 5' to the DNA sequence encoding the enzyme.

The secretory signal sequence may be that normally associated with the enzyme or may be from a gene encoding another secreted protein.

The procedures used to ligate the DNA sequences coding for the present enzyme, the promoter and optionally the terminator and/or secretory signal sequence, respectively, or to assemble these sequences by suitable PCR amplification schemes, and to insert them into suitable vectors containing the information necessary for replication or integration, are well known to persons skilled in the art (cf., for instance, Sambrook et al., op.cit.).

Host Cell

The present invention also relates to a recombinant host cell comprising the nucleic acid construct of the invention.

The DNA sequence encoding the present enzyme introduced into the host cell may be either homologous or heterologous to the host in question. If homologous to the host cell, i.e. produced by the host cell in nature, it will typically be operably connected to another promoter sequence or, if applicable, another secretory signal sequence and/or terminator sequence than in its natural environment. The term "homologous" is intended to include a DNA sequence encoding an enzyme native to the host organism in question. The term "heterologous" is intended to include a DNA sequence not expressed by the host cell in nature. Thus, the DNA sequence may be from another organism, or it may be a synthetic sequence.

The host cell into which the DNA construct or the recombinant vector of the invention is introduced may be any cell that is capable of producing the present enzyme and includes bacteria, yeast, fungi and higher eukaryotic cells including plants.

Examples of bacterial host cells which on cultivation are capable of producing the enzyme of the invention are gram-positive bacteria such as strains of *Bacillus*, such as strains of *B. subtilis, B. licheniformis, B. lentus, B. brevis, B. stearothermophilus, B. alkalophilus, B. amyloliquefaciens, B. coagulans, B. circulans, B. lautus, B. megaterium* or *B. thuringiensis*, in particular *B. lentus*, or strains of *Streptomyces*, such as *S. lividans* or *S. murinus*, or gram-negative bacteria such as *Escherichia coli*.

The transformation of the bacteria may be effected by protoplast transformation, electroporation, conjugation, or by using competent cells in a manner known per se (cf. Sambrook et al., supra).

When expressing the enzyme in bacteria such as *E. coli*, the enzyme may be retained in the cytoplasm, typically as insoluble granules (known as inclusion bodies), or may be directed to the periplasmic space by a bacterial secretion sequence. In the former case, the cells are lysed and the granules are recovered and denatured after which the enzyme is refolded by diluting the denaturing agent. In the latter case, the enzyme may be recovered from the periplasmic space by disrupting the cells, e.g. by sonication or osmotic shock, to release the contents of the periplasmic space and recovering the enzyme.

When expressing the enzyme in gram-positive bacteria such as *Bacillus* or *Streptomyces* strains, the enzyme may be retained in the cytoplasm, or may be directed to the extracellular medium by a bacterial secretion sequence. In the latter case, the enzyme may be recovered from the medium as described below.

In another embodiment of the invention, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds., *Soc. App. Bacteriol. Symposium Series* No. 9, 1980).

In a preferred embodiment, the yeast host cell is a *Candida, Hansenula, Kluyveromyces, Pichia, Saccharomyces, Schizosaccharomyces,* or *Yarrowia* cell.

In a most preferred embodiment, the yeast host cell is a *Saccharomyces carisbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium,* or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming Fusarium species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Method of Producing a Subtilase of the Invention

The present invention further relates to a method for producing a subtilase of the invention, the method comprising:

a) cultivating a recombinant host cell of the invention under conditions conducive to the production of the subtilase; and b) recovering the subtilase.

When an expression vector comprising a DNA sequence encoding the enzyme is transformed into a heterologous host cell, it is possible to enable heterologous recombinant production of the enzyme of the invention.

Thereby it is possible to make a highly purified subtilase composition, characterized in being free from homologous impurities.

In this context, homologous impurities mean any impurities (e.g. other polypeptides than the enzyme of the invention) that originate from the homologous cell where the enzyme of the invention is originally obtained from.

The medium used to culture the transformed host cells may be any conventional medium suitable for growing the host cells in question. The expressed subtilase may conveniently be secreted into the culture medium and may be recovered there from by well-known procedures including separating the cells from the medium by centrifugation or filtration, precipitating proteinaceous components of the medium by means of a salt such as ammonium sulfate, followed by chromatographic procedures such as ion exchange chromatography, affinity chromatography, or the like.

Use of a Sublitase of the Invention

A subtilase enzyme of the invention may be used for a number of industrial applications, in particular within the detergent industry. Thus, the present invention also relates to a cleaning or detergent composition, preferably a laundry or dish washing composition, comprising the subtilase enzyme of the invention.

Detergent Compositions Comprising the Sublitase Enzyme of the Invention:

In general, cleaning and detergent compositions are well described in the art and reference is made to WO 96/34946; WO 97/07202; WO 95/30011 for further description of suitable cleaning and detergent compositions.

Furthermore the examples herein demonstrate the improvements in performance on egg stains for the subtilases of the invention.

Detergent Compositions

The enzyme of the invention may be added to and thus become a component of a cleaning or detergent composition.

The detergent composition of the invention may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the subtilase enzyme of the invention. The detergent additive as well as the detergent composition may comprise one or more other enzymes such as another protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, preferably an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274 (BPN' numbering).

Preferred commercially available protease enzymes include Alcalase™, Savinase™, Primase™, Duralase™, Esperase™, and Kannase™ (Novozymes A/S), Maxatase™, Maxacal™, Maxapem™, Properase™, Purafect™, Purafect OxP™, FN2™, and FN3™ (Genencor International Inc.).

Lipases: Suitable lipases include those of bacterial or fungal origin. Chemically modified or protein engineered mutants are included. Examples of useful lipases include lipases from *Humicola* (synonym *Thermomyces*), e.g. from *H. lanuginosa* (*T. lanuginosus*) as described in EP 258 068 and EP 305 216 or from *H. insolens* as described in WO 96/13580, a *Pseudomonas* lipase, e.g. from *P. alcaligenes* or *P. pseudoalcaligenes* (EP 218 272), *P. cepacia* (EP 331 376), *P. stutzeri* (GB 1,372,034), *P. fluorescens, Pseudomonas* sp. strain SD 705 (WO 95/06720 and WO 96/27002), *P. wisconsinensis* (WO 96/12012), a *Bacillus* lipase, e.g. from *B. subtilis* (Dartois et al. (1993), Biochemica et Biophysica Acta, 1131, 253-360), *B. stearothermophilus* (JP 64/744992) or *B. pumilus* (WO 91/16422).

Other examples are lipase variants such as those described in WO 92/05249, WO 94/01541, EP 407 225, EP 260 105, WO 95/35381, WO 96/00292, WO 95/30744, WO 94/25578, WO 95/14783, WO 95/22615, WO 97/04079 and WO 97/07202.

Preferred commercially available lipase enzymes include Lipolase™ and Lipolase Ultra™ (Novozymes A/S).

Amylases: Suitable amylases (α and/or β) include those of bacterial or fungal origin. Chemically modified or protein engineered mutants are included. Amylases include, for example, α-amylases obtained from *Bacillus*, e.g. a special strain of *B. licheniformis*, described in more detail in GB 1,296,839.

Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444.

Commercially available amylases are Duramyl™, Termamyl™, FungaMyl™ and BAN™ (Novozymes A/S), Rapidase™ and Purastar™ (from Genencor International Inc.).

Cellulases: Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

Peroxidases/Oxidases: Suitable peroxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethylene glycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition of the invention may be in any convenient form, e.g. a bar, a tablet, a powder, a granule, a paste or a liquid. A liquid detergent may be aqueous, typically containing up to 70% water and 0-30% organic solvent, or non-aqueous.

The detergent composition typically comprises one or more surfactants, which may be nonionic including semipolar and/or anionic and/or cationic and/or zwitterionic. The surfactants are typically present at a level of from 0.1% to 60% by weight.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinylpyrrolidone), poly (ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system that may comprise a H2O2 source such as perborate or percarbonate that may be combined with a peracid-forming bleach activator such as tetraacetylethylenediamine or nonanoyloxybenzenesulfonate. Alternatively, the bleaching system may comprise peroxyacids of e.g. the amide, imide, or sulfone type.

The enzyme(s) of the detergent composition of the invention may be stabilized using conventional stabilizing agents, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

The enzyme of the invention may additionally be incorporated in the detergent formulations disclosed in WO 97/07202, which is hereby incorporated as reference.

The invention is described in further detail in the following examples that are not in any way intended to limit the scope of the invention as claimed.

In the detergent compositions, the abbreviated component identifications have the following meanings:

| | |
|---|---|
| LAS: | Sodium linear $C_{12}$ alkyl benzene sulfonate |
| TAS: | Sodium tallow alkyl sulphate |
| XYAS: | Sodium $C_{1X}$-$C_{1Y}$ alkyl sulfate |
| SS: | Secondary soap surfactant of formula 2-butyl octanoic acid |
| 25EY: | A $C_{12}$-$C_{15}$ predominantly linear primary alcohol condensed with an average of Y moles of ethylene oxide |
| 45EY: | A $C_{14}$-$C_{15}$ predominantly linear primary alcohol condensed with an average of Y moles of ethylene oxide |
| XYEZS: | $C_{1X}$-$C_{1Y}$ sodium alkyl sulfate condensed with an average of Z moles of ethylene oxide per mole |
| Non-ionic: | $C_{13}$-$C_{15}$ mixed ethoxylated/propoxylated fatty alcohol with an average degree of ethoxylation of 3.8 and an average degree of propoxylation of 4.5 sold under the trade name Plurafax LF404 by BASF GmbH |
| CFAA: | $C_{12}$-$C_{14}$ alkyl N-methyl glucamide |
| TFAA: | $C_{16}$-$C_{18}$ alkyl N-methyl glucamide |
| Silicate: | Amorphous Sodium Silicate ($SiO_2$:$Na_2O$ ratio = 2.0) |
| NaSKS-6: | Crystalline layered silicate of formula $\delta$-$Na_2Si_2O_5$ |
| Carbonate: | Anhydrous sodium carbonate |
| Phosphate: | Sodium tripolyphosphate |
| MA/AA: | Copolymer of 1:4 maleic/acrylic acid, average molecular weight about 80,000 |
| Polyacrylate: | Polyacrylate homopolymer with an average molecular weight of 8,000 sold under the trade name PA30 by BASF GmbH |
| Zeolite A: | Hydrated Sodium Aluminosilicate of formula $Na_{12}(AlO_2SiO_2)_{12} \cdot 27H_2O$ having a primary particle size in the range from 1 to 10 micrometers |
| Citrate: | Tri-sodium citrate dihydrate |
| Citric: | Citric Acid |
| Perborate: | Anhydrous sodium perborate monohydrate bleach, empirical formula $NaBO_2 \cdot H_2O_2$ |
| PB4: | Anhydrous sodium perborate tetrahydrate |
| Percarbonate: | Anhydrous sodium percarbonate bleach of empirical formula $2Na_2CO_3 \cdot 3H_2O_2$ |
| TAED: | Tetra-acetyl ethylene diamine |
| CMC: | Sodium carboxymethyl cellulose |
| DETPMP: | Diethylene triamine penta (methylene phosphonic acid), marketed by Monsanto under the trade name Dequest 2060 |
| PVP: | Polyvinylpyrrolidone polymer |
| EDDS: | Ethylene diamine-N,N'-disuccinic acid, [S,S] isomer in the form of the sodium salt |
| Suds Suppressor: | 25% paraffin wax, Mpt 50° C., 17% hydrophobic silica, 58% paraffin oil |
| Granular Suds Suppressor: | 12% Silicone/silica, 18% stearyl alcohol, 70% starch in granular form |
| Sulphate: | Anhydrous sodium sulphate |
| HMWPEO: | High molecular weight polyethylene oxide |
| TAE 25: | Tallow alcohol ethoxylate (25) |

DETERGENT EXAMPLE I

A granular fabric cleaning composition in accordance with the invention may be prepared as follows:

| | |
|---|---|
| Sodium linear $C_{12}$ alkyl benzene sulfonate | 6.5 |
| Sodium sulphate | 15.0 |
| Zeolite A | 26.0 |
| Sodium nitrilotriacetate | 5.0 |

-continued

| | |
|---|---|
| Enzyme | 0.1 |
| PVP | 0.5 |
| TAED | 3.0 |
| Boric acid | 4.0 |
| Perborate | 18.0 |
| Phenol sulfonate | 0.1 |
| Minors | up to 100% |

DETERGENT EXAMPLE II

A compact granular fabric cleaning composition (density 800 g/l) in accord with the invention may be prepared as follows:

| | |
|---|---|
| 45AS | 8.0 |
| 25E3S | 2.0 |
| 25E5 | 3.0 |
| 25E3 | 3.0 |
| TFAA | 2.5 |
| Zeolite A | 17.0 |
| NaSKS-6 | 12.0 |
| Citric acid | 3.0 |
| Carbonate | 7.0 |
| MA/AA | 5.0 |
| CMC | 0.4 |
| Enzyme | 0.1 |
| TAED | 6.0 |
| Percarbonate | 22.0 |
| EDDS | 0.3 |
| Granular suds suppressor | 3.5 |
| water/minors | Up to 100% |

DETERGENT EXAMPLE III

Granular fabric cleaning compositions in accordance with the invention that are especially useful in the laundering of coloured fabrics were prepared as follows:

| | | |
|---|---|---|
| LAS | 10.7 | — |
| TAS | 2.4 | — |
| TFAA | — | 4.0 |
| 45AS | 3.1 | 10.0 |
| 45E7 | 4.0 | — |
| 25E3S | — | 3.0 |
| 68E11 | 1.8 | — |
| 25E5 | — | 8.0 |
| Citrate | 15.0 | 7.0 |
| Carbonate | — | 10.0 |
| Citric acid | 2.5 | 3.0 |
| Zeolite A | 32.1 | 25.0 |
| Na-SKS-6 | — | 9.0 |
| MA/AA | 5.0 | 5.0 |
| DETPMP | 0.2 | 0.8 |
| Enzyme | 0.10 | 0.05 |
| Silicate | 2.5 | — |
| Sulphate | 5.2 | 3.0 |
| PVP | 0.5 | — |
| Poly (4-vinylpyridine)-N-Oxide/copolymer of vinyl-imidazole and vinyl-pyrrolidone | — | 0.2 |
| Perborate | 1.0 | — |
| Phenol sulfonate | 0.2 | — |
| Water/Minors | Up to 100% | |

DETERGENT EXAMPLE IV

Granular fabric cleaning compositions in accordance with the invention which provide "Softening through the wash" capability may be prepared as follows:

| | | |
|---|---|---|
| 45AS | — | 10.0 |
| LAS | 7.6 | — |
| 68AS | 1.3 | — |
| 45E7 | 4.0 | — |
| 25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| Perborate | 15.0 | — |
| Percarbonate | — | 15.0 |
| TAED | 5.0 | 5.0 |
| Smectite clay | 10.0 | 10.0 |
| HMWPEO | — | 0.1 |
| Enzyme | 0.10 | 0.05 |
| Silicate | 3.0 | 5.0 |
| Carbonate | 10.0 | 10.0 |
| Granular suds suppressor | 1.0 | 4.0 |
| CMC | 0.2 | 0.1 |
| Water/Minors | Up to 100% | |

DETERGENT EXAMPLE V

Heavy duty liquid fabric cleaning compositions in accordance with the invention may be prepared as follows:

| | | |
|---|---|---|
| LAS acid form | — | 25.0 |
| Citric acid | 5.0 | 2.0 |
| 25AS acid form | 8.0 | — |
| 25AE2S acid form | 3.0 | — |
| 25AE7 | 8.0 | — |
| CFAA | 5 | — |
| DETPMP | 1.0 | 1.0 |
| Fatty acid | 8 | — |
| Oleic acid | — | 1.0 |
| Ethanol | 4.0 | 6.0 |
| Propanediol | 2.0 | 6.0 |
| Enzyme | 0.10 | 0.05 |
| Coco-alkyl dimethyl | — | 3.0 |
| Smectite clay | — | 5.0 |
| PVP | 2.0 | — |
| Water/Minors | Up to 100% | |

Powder Automatic Dish Wash Composition I

| | |
|---|---|
| Non-ionic surfactant | 0.4-2.5% |
| Sodium metasilicate | 0-20% |
| Sodium disilicate | 3-20% |
| Sodium triphosphate | 20-40% |
| Sodium carbonate | 0-20% |
| Sodium perborate | 2-9% |
| Tetra acetyl ethylene diamine (TAED) | 1-4% |
| Sodium sulphate | 5-33% |
| Enzymes | 0.0001-0.1% |

Powder Automatic Dish Wash Composition II

| | |
|---|---|
| Non-ionic surfactant (e.g. alcohol ethoxylate) | 1-2% |
| Sodium disilicate | 2-30% |
| Sodium carbonate | 10-50% |
| Sodium phosphonate | 0-5% |
| Trisodium citrate dehydrate | 9-30% |
| Nitrilotrisodium acetate (NTA) | 0-20% |
| Sodium perborate monohydrate | 5-10% |
| Tetra-acetyl ethylene diamine (TAED) | 1-2% |
| Polyacrylate polymer (e.g. maleic acid/acrylic acid copolymer) | 6-25% |
| Enzymes | 0.0001-0.1% |
| Perfume | 0.1-0.5% |
| Water | 5-10 |

Powder Automatic Dish Wash Composition III

| | |
|---|---|
| Non-ionic surfactant | 0.5-2.0% |
| Sodium disilicate | 25-40% |
| Sodium citrate | 30-55% |
| Sodium carbonate | 0-29% |
| Sodium bicarbonate | 0-20% |
| Sodium perborate monohydrate | 0-15% |
| Tetra acetyl ethylene diamine (TAED) | 0-6% |
| Maleic acid/acrylic acid copolymer | 0-5% |
| Clay | 1-3% |
| Polyamino acids | 0-20% |
| Sodium polyacrylate | 0-8% |
| Enzymes | 0.0001-0.1% |

Powder Automatic Dish Wash Composition IV

| | |
|---|---|
| Non-ionic surfactant | 1-2% |
| Zeolite MAP | 15-42% |
| Sodium disilicate | 30-34% |
| Sodium citrate | 0-12% |
| Sodium carbonate | 0-20% |
| Sodium perborate monohydrate | 7-15% |
| Tetra acetyl ethylene diamine (TAED) | 0-3% |
| Polymer | 0-4% |
| Maleic acid/acrylic acid copolymer | 0-5% |
| Organic phosphonate | 0-4% |
| Clay | 1-2% |
| Enzymes | 0.0001-0.1% |
| Sodium sulphate | Balance |

Powder Automatic Dish Wash Composition V

| | |
|---|---|
| Non-ionic surfactant | 1-7% |
| Sodium disilicate | 18-30% |
| Trisodium citrate | 10-24% |
| Sodium carbonate | 12-20% |
| Monopersulphate (2 $KHSO_5 \cdot KHSO_4 \cdot K_2SO_4$) | 15-21% |
| Bleach stabilizer | 0.1-2% |
| Maleic acid/acrylic acid copolymer | 0-6% |
| Diethylene triamine pentaacetate, pentasodium salt | 0-2.5% |
| Enzymes | 0.0001-0.1% |
| Sodium sulphate, water | Balance |

Powder and Liquid Dish Wash Composition with Cleaning Surfactant System VI

| | |
|---|---|
| Non-ionic surfactant | 0-1.5% |
| Octadecyl dimethylamine N-oxide dehydrate | 0-5% |
| 80:20 wt. C18/C16 blend of octadecyl dimethylamine N-oxide dihydrate and hexadecyldimethyl amine N-oxide dehydrate | 0-4% |
| 70:30 wt.C18/C16 blend of octadecyl bis (hydroxy-ethyl) amine N-oxide anhydrous and hexadecyl bis (hydroxyethyl)amine N-oxide anhydrous | 0-5% |
| $C_{13}$-$C_{15}$ alkyl ethoxysulfate with an average degree of ethoxylation of 3 | 0-10% |
| $C_{12}$-$C_{15}$ alkyl ethoxysulfate-with an average degree of ethoxylation of 3 | 0-5% |
| $C_{13}$-$C_{15}$ ethoxylated alcohol with an average degree of ethoxylation of 12 | 0-5% |
| A blend of $C_{12}$-$C_{15}$ ethoxylated alcohols with an average degree of ethoxylation of 9 | 0-6.5% |
| A blend of $C_{13}$-$C_{15}$ ethoxylated alcohols with an average degree of ethoxylation of 30 | 0-4% |
| Sodium disilicate | 0-33% |
| Sodium tripolyphosphate | 0-46% |
| Sodium citrate | 0-28% |
| Sodium acid | 0-29% |
| Sodium carbonate | 0-20% |
| Sodium perborate monohydrate | 0-11.5% |
| Tetra-acetyl ethylene diamine (TAED) | 0-4% |
| Maleic acid/acrylic acid copolymer | 0-7.5% |
| Sodium sulphate | 0-12.5% |
| Enzymes | 0.0001-0.1% |

Non-aqueous Liquid Automatic Dishwashing Composition VII

| | |
|---|---|
| Liquid non-ionic surfactant (e.g. alcohol ethoxylates) | 2.0-10.0% |
| Alkali metal silicate | 3.0-15.0% |
| Alkali metal phosphate | 20.0-40.0% |
| Liquid carrier selected from higher glycols, polyglycols, polyoxides, glycol ethers | 25.0-45.0% |
| Stabilizer (e.g. a partial ester of phosphoric acid and a $C_{16}$-$C_{18}$ alkanol) | 0.5-7.0% |
| Foam suppressor (e.g. silicone) | 0-1.5% |
| Enzymes | 0.0001-0.1% |

Non-aqueous Liquid Dishwashing Composition VIII

| | |
|---|---|
| Liquid non-ionic surfactant (e.g. alcohol ethoxylates) | 2.0-10.0% |
| Sodium silicate | 3.0-15.0% |
| Alkali metal carbonate | 7.0-20.0% |
| Sodium citrate | 0.0-1.5% |
| Stabilizing system (e.g. mixtures of finely divided silicone and low molecular weight dialkyl polyglycol ethers) | 0.5-7.0% |
| Low molecule weight polyacrylate polymer | 5.0-15.0% |
| Clay gel thickener (e.g. bentonite) | 0.0-10.0% |
| Hydroxypropyl cellulose polymer | 0.0-0.6% |
| Enzymes | 0.0001-0.1% |
| Liquid carrier selected from higher lycols, polyglycols, polyoxides and glycol ethers | Balance |

Thixotropic Liquid Automatic Dishwashing Composition IX

| | |
|---|---|
| $C_{12}$-$C_{14}$ fatty acid | 0-0.5% |
| Block co-polymer surfactant | 1.5-15.0% |

-continued

| | |
|---|---|
| Sodium citrate | 0-12% |
| Sodium tripolyphosphate | 0-15% |
| Sodium carbonate | 0-8% |
| Aluminium tristearate | 0-0.1% |
| Sodium cumene sulfonate | 0-1.7% |
| Polyacrylate thickener | 1.32-2.5% |
| Sodium polyacrylate | 2.4-6.0% |
| Boric acid | 0-4.0% |
| Sodium formate | 0-0.45% |
| Calcium formate | 0-0.2% |
| Sodium n-decydiphenyl oxide disulfonate | 0-4.0% |
| Monoethanol amine (MEA) | 0-1.86% |
| Sodium hydroxide (50%) | 1.9-9.3% |
| 1,2-Propanediol | 0-9.4% |
| Enzymes | 0.0001-0.1% |
| Suds suppressor, dye, perfumes, water | Balance |

Liquid Automatic Dishwashing Composition X

| | |
|---|---|
| Alcohol ethoxylate | 0-20% |
| Fatty acid ester sulfonate | 0-30% |
| Sodium dodecyl sulphate | 0-20% |
| Alkyl polyglycoside | 0-21% |
| Oleic acid | 0-10% |
| Sodium disilicate monohydrate | 18-33% |
| Sodium citrate dehydrate | 18-33% |
| Sodium stearate | 0-2.5% |
| Sodium perborate monohydrate | 0-13% |
| Tetra-acetyl ethylene diamine (TAED) | 0-8% |
| Maleic acid/acrylic acid copolymer | 4-8% |
| Enzymes | 0.0001-0.1% |

Liquid Automatic Dishwashing Composition Containing Protected Bleach Particles XI

| | |
|---|---|
| Sodium silicate | 5-10% |
| Tetra potassium pyrophosphate | 15-25% |
| Sodium triphosphate | 0-2% |
| Potassium carbonate | 4-8% |
| Protected bleach particles, e.g. chlorine | 5-10% |
| Polymeric thickener | 0.7-1.5% |
| Potassium hydroxide | 0-2% |
| Enzymes | 0.0001-0.1% |
| Water | Balance |

XII: Automatic dishwashing compositions as described in I, II, III, IV, VI and X, wherein perborate is replaced by percarbonate.

XIII: Automatic dishwashing compositions as described in I-VI, which additionally contain a manganese catalyst. The manganese catalyst may, e.g., be one of the compounds described in "Efficient manganese catalysts for low-temperature bleaching", *Nature*, (1994), 369, 637-639.

Materials And Methods

Proteolytic Activity

In the context of this invention, proteolytic activity is expressed in Kilo NOVO Protease Units (KNPU). The activity is determined relatively to an enzyme standard (SAVINASE®), and the determination is based on the digestion of a dimethyl casein (DMC) solution by the proteolytic enzyme at standard conditions, i.e. 50° C., pH 8.3, 9 min. reaction time, 3 min. measuring time. A folder AF 220/1 is available upon request to Novozymes A/S, Denmark, which folder is hereby included by reference.

A GU is a Glycine Unit, defined as the proteolytic enzyme activity that under standard conditions during a 15 minutes' incubation at 40° C., with N-acetyl casein as substrate produces an amount of $NH_2$-group equivalent to 1 mmole of glycine.

Enzyme activity can also be measured using the PNA assay, according to reaction with the soluble substrate succinyl-alanine-alanine-proline-phenyl-alanine-para-nitrophenol, which is described in the Journal of American Oil Chemists Society, Rothgeb, T. M., Goodlander, B. D., Garrison, P. H., and Smith, L. A., (1988).

EXAMPLE 1

Construction and Expression of Subtilases According to the Invention

Example 1 covers both SEQ ID NO:2 and SEQ ID NO:4. It is to be understood that the term SEQ ID NO:2 at any time can be replaced by the term SEQ ID NO:4.

The subtilisins having the amino acid sequence shown in SEQ ID NO:2 was located in vector pjRoC112, which is very similar to plasmid pKH400 (previously described in WO 98/41623). The plasmids are identical outside the regions encoding the mature subtilisin, i.e. the origin of replication; the cat gene conferring resistance towards chloramphenicol, the promoter directing the initiation of transcription of the subtilisin and the pre/pro regions from Savinase®) are identical in these plasmids. Differences are only found within the part of the gene encoding the mature subtilisin.

This plasmid replicates both in *E. coli* and in *Bacillus subtilis*. In *Bacillus subtilis* the subtilisin according to the invention was expressed from this plasmid. Fermentation and purification of the protease is described below.

PKH400 was constructed from pJS3 (*E. coli*-*B. subtilis* shuttle vector containing a synthetic gene encoding for subtilase 309 (Savinase®) as described by J. Schiødt et al. in *Protein and Peptide Letters*, 3, 39-44 (1996)) by introducton of two BamHI sites at positions 1841 and 3730.

The mature gene has been subcloned into plasmid pzero-2 (Invitrogen, Groningen, The Netherlands). An approximately 1240 bp Pmel-BamHI fragment containing the complete mature region of the subtilase having the amino acid sequence shown in SEQ ID NO:2 was ligated with vector pZero2 and digested with restriction endonucleases BamHI-EcoRV. The ligation mixture was transformed into competent *E. coli* cells. Transformants were analysed by PCR to verify the presence of the inserted fragment and the part of this fragment encoding the mature subtilisin was sequenced. The resulting plasmid, denoted pTVB364, was deposited on 10 Feb. 2000 at DSMZ and was given the accession number DSM 13306.

Fermentation

Fermentations for the production of subtilase enzymes were performed at 30° C. on a rotary shaking table (300 r.p.m.) in 500 ml baffled Erlenmeyer flasks containing 100 ml BPX medium for 5 days.

Consequently, in order to make e.g. a 2 liter broth 20 Erlenmeyer flasks were fermented simultaneously.

Media:

| BPX Medium Composition (per litre) | |
|---|---|
| Potato starch | 100 g |
| Ground barley | 50 g |

| BPX Medium Composition (per litre) | |
| --- | --- |
| Soybean flour | 20 g |
| Na2HPO4 × 12H2O | 9 g |
| Pluronic | 0.1 g |
| Sodium caseinate | 10 g |

The starch in the medium was liquefied with α-amylase and the medium was sterilized by heating at 120° C. for 45 minutes. After sterilization the pH of the medium was adjusted to 9 by addition of NaHCO3 to 0.1 M.

Purification

This procedure relates to purification of a 2 liter scale fermentation for the production of the subtilases of the invention in a *Bacillus* host cell.

Approximately 1.6 liters of fermentation broth was centrifuged at 5000 rpm for 35 minutes in 1 liter beakers. The supernatants were adjusted to pH 6.5 using 10% acetic acid and filtered on Seitz Supra S100 filter plates.

The filtrates were concentrated to approximately 460 ml using an Amicon CH2A UF unit equipped with an Amicon S1Y10 UF cartridge. The UF concentrate was centrifuged and filtered at room temperature prior to absorption on a Bacitracin affinity column at pH 7. The subtilase was eluted from the Bacitracin column at room temperature using 25% 2-propanol and 1 M sodium chloride in a buffer solution with 0.01 dimethylglutaric acid, 0.1 M boric acid and 0.002 M calcium chloride adjusted to pH 7.

The fractions with protease activity from the Bacitracin purification step were combined and applied to a 750 ml Sephadex G25 column (5 cm diameter) equilibrated with a buffer containing 0.01 dimethylglutaric acid, 0.2 M boric acid and 0.002 m calcium chloride adjusted to pH 6.5.

Fractions with proteolytic activity from the Sephadex G25 column were combined and applied to a 150 ml CM Sepharose CL 6B cation exchange column (5 cm diameter) equilibrated with a buffer containing 0.01 M dimethylglutaric acid, 0.2 M boric acid, and 0.002 M calcium chloride adjusted to pH 6.5.

The protease was eluted using a linear gradient of 0-0.1 M sodium chloride in 2 liters of the same buffer.

In a final purification step, protease-containing fractions from the CM Sepharose column were combined and concentrated in an Amicon ultra filtration cell equipped with a GR81PP membrane (from the Danish Sugar Factories Inc.).

By using the techniques mentioned above for the construction and fermentation, and the above isolation procedure, the novel subtilase having the amino acid sequence set forth in SEQ ID NO:2 was produced and isolated.

EXAMPLE 2

The "Model Detergent Wash Performance Test"

In order to asses the wash performance of subtilases in a standard detergent composition, standard washing experiments may be performed using the below experimental conditions:

| | |
| --- | --- |
| Detergent: | Model detergent |
| Detergent dosage | 4.0 g/l |
| pH | 10.1 |
| Wash time | 20 min |
| Temperature: | 30° C. |
| Water hardness: | 15°dH |
| Enzyme concentration: | 10 nm (in the detergent solution) |
| Test system: | 10 ml beakers with a stirring rod |
| Textile/volume: | 5 textile pieces (Ø 2.5 cm)/50 ml detergent solution |
| Test material: | WEK10N (egg stains) |

The composition of the model detergent is as follows:

| | |
| --- | --- |
| 6.2% | LAS (Nansa 80S) |
| 2% | Sodium salt of $C_{16}$-$C_{18}$ fatty acid |
| 4% | Non-ionic surfactant (Plurafax LF404) |
| 22% | Zeolite P |
| 10.5% | $Na_2CO_3$ |
| 4% | $Na_2Si_2O_5$ |
| 2% | Carboxymethylcellulose (CMC) |
| 6.8% | Acrylate liquid CP5 40% |
| 20% | Sodium perborate (empirical formula $NaBO_2 \cdot H_2O_2$) |
| 0.2% | EDTA |
| 21% | $Na_2SO_4$ |
| | Water (balance) | pH of the detergent solution is adjusted to 10.1 by addition of HCl or NaOH. Water hardness is adjusted to 15° dH by addition of $CaCl_2$ and $MgCl_2$ ($Ca^{2+}$:$Mg^{2+}$=4:1) to the test system. After washing the textile pieces are flushed in tap water and air-dried.

Measurement of the reflectance ($R_{subsilase}$) on the test material is performed at 460 nm using a Macbeth ColorEye 7000 photometer (Macbeth, Division of Kollmorgen Instruments Corporation, Germany). The measurements are performed in accordance with the manufacturer's protocol.

In order to determine a blank value, a similar wash experiment is performed without addition of enzyme. The subsequent measurement of the reflectance ($R_{blank}$) is performed as described right above.

A reference experiment is then performed as described above, wherein the wash performance of Savinase® is tested. The subsequent measurement of the reflectance ($R_{savinase}$) is performed as described right above.

The wash performance is evaluated by means of the Performance Factor (P) which is defined in accordance with the below formula:

$$P = (R_{subtilase} - R_{blank}) - (R_{savinase} - R_{blank})$$
$$= R_{subtilase} - R_{savinase}.$$

EXAMPLE 3

The Full Scale Automatic Dish Washing (ADW) Test

The performance of the subtilase of the invention in full scale ADW is tested in a household dish wash composition using standard conditions. The soil used is an egg/milk mixture coated on a steel plate. Further, a ballast soil containing various foodstuffs is added.

Example:

| | |
|---|---|
| Detergent: | Commercial or model detergent. |
| Detergent dosage | 5.0 g/l |
| pH | As is. |
| Water hardness: | As is. |
| Temperature: | 50° C. or 55° C. |
| Enzyme concentration: | 10 nM to 230 nM, based on the total volume of wash water in the machine. |
| Test method: | Egg/milk or egg yolk soiling on steel plates as described below. |
| Machine: | Bosch or other commercially available. |
| Wash program: | |

Tap Water is Used; the Following Steps are Applied:

| Step | Time (seconds) | Temperature |
|---|---|---|
| Main wash | 1200[1] | 50° C.[2] |
| Rinse | 300[1] | 39° C.[2] |
| Dry | 1530 | 65° C. |

[1] Heating of tap water takes place during the indicated time interval.
[2] Final temperature upon heating of tap water.

Egg/Milk Soiling for Full Scale ADW Test

Materials:

220 ml full cream milk 15 eggs, medium size

Steel plates, diameter 18 cm

The dish wash composition is heated at 85° C. for 5 minutes in a microwave oven in order to inactivate enzyme activity in the composition.

Soiling of Steel Plates:

220 ml full cream milk is mixed with 15 raw eggs in a Braun UK 20 kitchen machine for 2 minutes. After sieving, stainless steel plates are soiled in the mixture by immersion.

The plates are dried overnight at room temperature in an upright position. The dried plates are then heated at 120° C. for 45 minutes in order to denature the proteins on the surface.

Egg Yolk Soiling for Full Scale ADW Test.

Materials:

3 dL pasteurized egg yolk.

Steel plates, diameter 18 cm

The dish wash composition is heated at 85° C. for 5 minutes in a microwave oven in order to inactivate enzyme activity in the composition.

Soiling of Steel Plates:

The steel plates are weighed on a balance giving 3 decimals.

Approx. 3 dL pasteurized egg yolk is mixed thoroughly and sieved through a kitchen screen.

The egg yolk broth is rolled onto the plates in a thin layer, e.g. using a paint roller. This is done twice (without drying, in between and with the roller dipped in egg yolk also the second time).

The resulting layer of egg yolk should be around 1 g.

The plates are left to dry for minimum 4 hours at room temperature.

The soiled plates and the racks are then lowered into boiling demineralised water for precisely 30 seconds.

The plates are left to dry for 30 minutes at room temperature.

After drying at room temperature the plates are dried in an oven at 80° C. for 30 minutes.

The plates are left to cool at room temperature for 30-60 minutes after which they are weighed again.

Upon washing and drying at room temperature the plates are dried in the oven at 80° C. for 30 min.

Again after cooling at room temperature for 30-60 minutes the plates are weighed.

ADW Experiments

For each experiment, 10 soiled plates are washed in accordance with conditions listed above. In addition to the soiled plates, the machine is filled up with 10 porcelain plates, 4 glasses, 4 cups and 16 pieces of cutlery.

Furthermore, 50 g of ballast slurry is added to the machine. The composition of the slurry is as follows:

3000 g are made, and the following components are weighed out:

| Step | Materials | Dosage (g) |
|---|---|---|
| 1 | Margarine | 189 |
| | Lard | 189 |
| | Deep-Fry Oil | 189 |
| | Gravy Powder | 51 |
| 2 | Rapeseed Oil | 948 |
| | Egg | 474 |
| 3 | Ketchup | 189 |
| | Mustard | 189 |
| 4 | Double Cream, 38% fat | 282 |
| | Full-Cream Milk, 3.5% fat | 189 |
| 5 | Potato Flour | 66 |
| | Wheat Flour | 18 |
| | Quark powder | 18 |
| | Benzoic Acid | 9 |

1. Margarine, lard and deep-fry oil are melted at low temperature. Afterwards sieved gravy powder is added—under good stirring—and is cooled down to 40° C.
2. Rapeseed oil and egg are mixed.
3. Ketchup and mustard are added into the oil/egg mass followed by 5 minutes mixing.
4. The under 1) produced fat/gravy (cooled) is slowly added to the mixture produced in 3) and mixed for further 5 minutes.
5. Double cream and full-cream milk are added the mixture and mixed for 5 minutes.
6. The last flours and powders (step 5 in the table) is added. The ballast slurry is mixed to a smooth mass.
7. The Ballast slurry is weighed out in portions of 50 g.

Measurements and Calculations for Egg/Milk

The light reflection values (R-values) are measured at six different locations on the plates using a Minolta Chroma Meter (Type: CR-300). Measurements are made on clean plates ($R_{clean}$), on soiled plates after heating ($R_{soiled}$) and on plates after wash ($R_{after\ wash}$). The removed protein film (% RPF) is calculated according to the below formula:

$$\% RPF = 100\% \times (R_{after\ wash} - R_{soiled})/(R_{clean} - R_{soiled})$$

Measurements and Calculations for Egg Yolk

Performance data originate from gravimetric measurements of the steel plates as clean, soiled and washed. The performance is calculated as:

$$\% \text{ Removed Protein Film } (\% RPF) = \frac{(Weight_{soiled} - Weight_{washed}) \times 100}{Weight_{soiled} - Weight_{clean}}$$

Data Analysis:

% RPF is fitted as a function of mg enzyme protein added. The data are fitted by means of a four-parameter logistic model that can be written as:

$$F(z) = Y_0 + V_{max} * C^\lambda / (k_s^{80} + C^\lambda)$$

Where F(z) is the response calculated from $Y_0$ as the intercept, $Y_0 + V_{max}$ being maximum response, C the enzyme dosage and $k_s$ being the half-saturation value. $\lambda$ is the steepness parameter that in a Michaelis-Menten model is equal 1, but here it is equal or different from one as we are allowing S-shaped curves to be fitted.

Each curve fit is compared to the performance of the reference enzyme.

EXAMPLE 4

Mini Scale Automatic Dish Washing (ADW Mini Wash)

Description of ADW Mini-wash

The mini-wash is developed as a computerized robot. Each robot carries a frame with 8 racks. Each rack contains 6 pieces of 35×45 mm steel plates to be soiled and washed. If needed the 6 positions can represent the six points in the dosage range, e.g. 0-20-40-75-100-160 nM enzyme as shown below. One wash unit consists of two plates, egg yolk and egg/milk soiled respectively, and a thermostated vessel with 150 ml wash float. A robot operates on 24 vessels at a time As mentioned two racks are needed for each enzyme to be tested, one being soiled with egg yolk the other egg/milk. The reference enzyme is included at each run and each enzyme dosage is repeated twice.

The setup is schematically depicted in FIG. 2.

The Egg/Milk Soil is Prepared as Follows:

10 eggs+167 ml of milk are blended 2 min at low speed in a food processor. The mixture is sieved through a disposable cloth before use. Racks are mounted with mini plates and dipped into the sieved soil. The plates are placed upright on an absorbing table cover. They are left to dry for 4 hours or until next day where they are denatured by heat treatment in hot air ovens at 120° C. for 35 minutes.

The Egg Yolk Soil is Prepared as Follows:

20 yolks ~400 ml pasteurized catering yolk (~420 g)+167 ml deionised water is blended 2 minutes at lowest speed in a food processor then sieved through a disposable cloth before use. Racks are mounted with mini plates and dipped into the sieved soil. The plates are placed upright on an absorbing table cover. They are left to dry for 4 hours or until next day where they are denatured 30 sec. in boiling water. After denaturing the plates are heat treated in hot air ovens at 80° C. for 30 minutes.

Detergents

Detergents for wash performance tests of the shuffled proteases of the invention can be obtained by purchasing fully formulated commercial detergents at the market and subsequently inactivate the enzymatic components by heat treatment (5 minutes at 85° C. in aqueous solution). Moreover a commercial detergent base without enzymes can be purchased directly from the manufacturer. Further a suitable model detergent can be purchased and used for wash performance tests.

The proteases may be tested in a model detergent composition comprising

| | |
|---|---|
| Sodium Tripolyphosphat | 23.0% |
| Sodium Citrate Dihydrate | 22.3% |
| Sodium Perborate Monohydrate | 6.0% |
| Tetraacetyl Ethylendiamine | 2.0% |
| Sodium Disilicate (noncrystaline) | 5.0% |
| Linear Fatty Alcohol Ethoxylate | 2.0% |
| (non-ionic surfactant, low foaming) | |
| Maleic acid/Acrylic acid copolymer | 4.0% |
| (Sodium salt, 50% active on Sodium Carbonate) | |
| Sodium Carbonate, anhydrous add to | 100% |

The wash floats are prepared by mixing $CaCl_2$, $MgSO_4$ and $NaHCO_3$ deionised water to make up the various water hardness values. Detergent is added: 18-25 g/4L.

Evaluation:

Performance data originate from gravimetric measurements of the steel plates as clean, soiled and washed. The performance is calculated as:

$$\% \text{ Removed Protein Film } (\% RPF) = \frac{(Weight_{soiled} - Weight_{washed}) \times 100}{Weight_{soiled} - Weight_{clean}}$$

Data Analysis

% RPF is fitted as a function of mg enzyme protein added. The data are fitted to the four-parameter logistic model that can be written as:

$$F(z) = Y_0 + V_{max} * C^\lambda / (k_s^\lambda + C^\lambda)$$

Where F(z) is the response calculated from $Y_0$ as the intercept, $Y_O + V_{max}$ being maximum response, C the enzyme dosage and $k_s$ being the half-saturation value. $\lambda$ is the steepness parameter that in a Michaelis-Menten model is equal 1, but here it is equal or different from one as we are allowing S-shaped curves to be fitted. Each curve fit is compared to the performance of the reference enzyme.

Using the above test method on egg yolk soil the results shown in FIG. 3 were obtained (% RPF as a function of mg enzyme protein). As it appears, the subtilases according to the invention exhibits improved wash performance on egg stains in comparison to SEQ ID NO:6 (named PH004).

EXAMPLE 5

Automatic Mechanical Stress Assay (AMSA)

Description of AMSA-test Method:

Washing experiments are performed in order to asses the wash performance of selected shuffled protease variants in detergent compositions. The proteases of the present application are tested using the Automatic Mechanical Stress Assay (AMSA). With the AMSA, the wash performance of a large quantity of small volume enzyme-detergent solutions can be examined. The AMSA plate has a number of slots for test solutions and a lid firmly squeezing the textile swatch to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" at page 23-24.

The experiment was conducted under the experimental conditions specified below:

| | |
|---|---|
| Commercial detergent base | European 3in1 ADW type |
| Detergent dosage | 5-5.5 g/L |
| Test solution volume | 160 µL |
| pH | As is |
| Wash time | 20 minutes |
| Temperature | 50° C. |
| Water hardness | 25°dH |
| Enzyme concentration in test solution | 0.25 mg/L, 0.5 mg/L, 1 mg/L, and 2.5 mg/L for wfk10N; 1 mg/L, 2.5 mg/L, 4 mg/L, and 6 mg/L for denatured wfk10N. |
| Test material | Wfk10N, or denatured wfk10N |

Water hardness was adjusted to 25° dH by addition of $CaCl_2$, $MgCl_2$, and $NaHCO_3$ ($Ca^{2+}:Mg^{2+}=4:1$) to the test system. After washing the textile pieces were flushed in tap water and dried.

The performance of the enzyme variant is measured as the brightness of the colour of the textile samples washed with that specific protease. Brightness can also be expressed as the intensity of the light reflected from the textile sample when illuminated with white light. When the textile is stained the intensity of the reflected light is lower, than that of a clean textile. Therefore the intensity of the reflected light can be used to measure wash performance of a shuffled protease.

Colour measurements are made with a professional flatbed scanner (PFU DL2400pro, obtainable from: J. M. Thomsen, Dorfgade 2, Dorf, Dronninglund, DK-9330), which is used to capture an image of the washed textile samples. The scans are made with a resolution of 200 dpi and with an output colour dept of 24 bits. In order to get accurate results, the scanner is frequently calibrated with a Kodak reflective IT8 target.

To extract a value for the light intensity from the scanned images, a special designed software application is used (Novozymes Color Vector Analyzer). The program retrieves the 24 bit pixel values from the image and converts them into values for red, green and blue (RGB). The intensity value (Int) is calculated by adding the RGB values together as vectors and then taking the length of the resulting vector:

$$Int=\sqrt{r^2+g^2+b^2}.$$

Detergents

Detergents for wash performance tests of the shuffled proteases of the invention can be obtained by purchasing fully formulated commercial detergents at the market and subsequently inactivate the enzymatic components by heat treatment (5 minutes at 85° C. in aqueous solution). Moreover a commercial detergent base without enzymes can be purchased directly from the manufacturer. Further a suitable model detergent can be purchased and used for wash performance tests.

The proteases may be tested in a model detergent composition comprising

| | |
|---|---|
| Sodium Tripolyphosphate | 23.0% |
| Sodium Citrate Dihydrate | 22.3% |
| Sodium Perborate Monohydrate | 6.0% |
| Tetraacetyl Ethylendiamine | 2.0% |
| Sodium Disilicate (noncrystaline) | 5.0% |
| Linear Fatty Alcohol Ethoxylate (non-ionic surfactant, low foaming) | 2.0% |
| Maleic acid/Acrylic acid copolymer (Sodium salt, 50% active on Sodium Carbonate) | 4.0% |
| Sodium Carbonate, anhydrous add to | 100% |

Textiles:

Standard textile pieces are obtained from wfk-Cleaning Technology Research Institute, Christenfeld 10, D-41379 Brüggen-Bracht, Germany. Especially type wfk10N (cotton textile stained with egg/pigment), wfk10eggEG (cotton textile stained with egg yolk). Denaturation of wfk10N occurs in an autoclave.

Using the above test method in combination with a commercially available detergent the results shown in FIG. 4 were obtained. As it appears, the subtilases according to the invention exhibits improved wash performance on egg stains in comparison to the protease with SEQ ID NO:6 (named PH004).

Deposit of Biological Material

The following biological material has been deposited under the terms of the Budapest Treaty with the Deutsche Sammlung von Mikroorganismen und Zellkulturen GmbH, Mascheroder Weg 1 B, D-38124 Braunschweig, Germany, and given the following accession numbers:

| Deposit | Accession Number | Date of deposit |
|---|---|---|
| E. coli MT173 | DSM 15574 | 16 Apr. 2003 |
| E. coli MT173 | DSM 15575 | 16 Apr. 2003 |

The invention claimed is:

1. A subtilase enzyme being selected from the group consisting of
   (a) a subtilase having an amino acid sequence that has at least 99.63% identity with the amino acid sequence shown as amino acids 1 to 269 of SEQ ID NO:2; and
   (b) a subtilase encoded by the subtilase encoding part of the polynucleotide cloned into the plasmid fragment present in *Escherichia coli* MT173 DSM 15575, or a variant thereof having at least 99.63% identity to said subtilase.

2. The subtilase of claim 1, which consists of the amino acid sequence of amino acids 1 to 269 of SEQ ID NO:2.

3. The subtilase of claim 1, wherein the subtilase is a variant of a subtilase having the sequence of amino acids 1 to 269 of SEQ ID NO:2 comprising a substitution, deletion, or insertion of one amino acid.

4. The subtilase of claim 3, comprising one modification in one of the positions 27, 36, 56, 76, 87, 95, 96, 97, 98, 99, 100, 101, 102, 103, 104, 120, 123, 159, 167, 170, 206, 218, 222, 224, 232, 235, 236, 245, 248, 252 and 274, where the positions are numbered according to alignment with the amino acid sequence of subtilisin BPN' set forth in SEQ ID NO:5.

5. The subtilase of claim 4, wherein the modification is selected from the group consisting of K27R, *36D, S56P, N76D, S87N, G97N, S101G, S103A, V104A, V104I, V104N, V104Y, H120D, N123S, G159D, Y167, R170, Q206E, N218S, M222S, M222A, T224S, A232V, K235L, Q236H, Q245R, N248D, N252K and T274A, where the positions are numbered according to alignment with the amino acid sequence of subtilisin BPN' set forth in SEQ ID NO:5.

6. A cleaning or detergent composition comprising the subtilase of claim 1.

7. The composition of claim 6 which additionally comprises a cellulase, lipase cutinase, oxidoreductase, another protease, an amylase or a mixture thereof.

8. A method for cleaning or dish washing, washing a hard surface or laundry, comprising contacting the hard surface or the laundry with the composition of claim 6.

9. A method for removal of egg stains from a hard surface or from laundry, comprising contacting an egg stain-containing hard surface or an egg stain-containing laundry with the composition of claim 6.

10. An isolated polynucleotide comprising a polynucleotide that encodes the subtilase of claim 1.

11. A nucleic acid construct comprising the nucleic acid sequence of claim 10 operably linked to one or more control sequences capable of directing the expression of the subtilase in a suitable host.

12. A recombinant host cell comprising the nucleic acid construct of claim 11.

13. A method for producing a subtilase, comprising:
   (a) cultivating a recombinant host cell of claim 12 under conditions conducive to the production of the subtilase; and
   (b) recovering the subtilase.

* * * * *

SEQUENCE LISTING

```
<160> NUMBER OF SEQ ID NOS: 6

<210> SEQ ID NO 1
<211> LENGTH: 807
<212> TYPE: DNA
<213> ORGANISM: Artificial
<220> FEATURE:
<223> OTHER INFORMATION: Prepared by DNA-shuffling
```

```
<220> FEATURE:
<221> NAME/KEY: CDS
<222> LOCATION: (1)..(807)
<223> OTHER INFORMATION: prepared by DNA shuffling

<400> SEQUENCE: 1 gcg caa tcg gta cca tgg gga att agc cgt gtg caa gcc cca gct gcc      48
Ala Gln Ser Val Pro Trp Gly Ile Ser Arg Val Gln Ala Pro Ala Ala
1               5                   10                  15 cat aac cgt gga ttg aca ggt tct ggt gta aaa gtt gct gtc ctc gat      96
His Asn Arg Gly Leu Thr Gly Ser Gly Val Lys Val Ala Val Leu Asp
            20                  25                  30 aca ggg ata tcc act cat cca gat cta aat att cgt ggt ggc gca agc     144
Thr Gly Ile Ser Thr His Pro Asp Leu Asn Ile Arg Gly Gly Ala Ser
        35                  40                  45 ttt gta cca ggg gaa ccg tcg act caa gat ggg aac ggg cat ggg acg     192
Phe Val Pro Gly Glu Pro Ser Thr Gln Asp Gly Asn Gly His Gly Thr
    50                  55                  60 cac gtt gca gga acg att gcg gct ctt gat aat tca atc ggt gtg att     240
His Val Ala Gly Thr Ile Ala Ala Leu Asp Asn Ser Ile Gly Val Ile
65                  70                  75                  80 ggt gtg gca cca agt gct gat cta tac gct gta aaa gta ctt gga gca     288
Gly Val Ala Pro Ser Ala Asp Leu Tyr Ala Val Lys Val Leu Gly Ala
                85                  90                  95 aat ggt aga gga agc gtt agt gga att gct caa ggt cta gag tgg gct     336
Asn Gly Arg Gly Ser Val Ser Gly Ile Ala Gln Gly Leu Glu Trp Ala
            100                 105                 110 gca gcg aat aac atg cat att gct aac atg agt ctc ggt agt gat gca     384
Ala Ala Asn Asn Met His Ile Ala Asn Met Ser Leu Gly Ser Asp Ala
        115                 120                 125 cct agt act aca ctt gag cgt gca gtc aac tac gcg aca agc caa ggt     432
Pro Ser Thr Thr Leu Glu Arg Ala Val Asn Tyr Ala Thr Ser Gln Gly
    130                 135                 140 gta cta gtt att gca gcg act ggt aac aac ggt tct ggt tca gtt ggc     480
Val Leu Val Ile Ala Ala Thr Gly Asn Asn Gly Ser Gly Ser Val Gly
145                 150                 155                 160 tat cct gct cgt tat gca aac gca atg gct gta gga gcg act gac caa     528
Tyr Pro Ala Arg Tyr Ala Asn Ala Met Ala Val Gly Ala Thr Asp Gln
                165                 170                 175 aac aac aga cgt gca aac ttt tct cag tac ggt aca gga att gac atc     576
Asn Asn Arg Arg Ala Asn Phe Ser Gln Tyr Gly Thr Gly Ile Asp Ile
            180                 185                 190 gta gca cct gga gtt aac gta caa agt acg tat cca gga aac cgt tat     624
Val Ala Pro Gly Val Asn Val Gln Ser Thr Tyr Pro Gly Asn Arg Tyr
        195                 200                 205 gtg agt atg aat ggt aca tct atg gcc act cca cac gtc gcc ggc gtc     672
Val Ser Met Asn Gly Thr Ser Met Ala Thr Pro His Val Ala Gly Val
    210                 215                 220 gcc gcc ctt gtt aaa caa aag aac cca tct tgg tct aat gta caa att     720
Ala Ala Leu Val Lys Gln Lys Asn Pro Ser Trp Ser Asn Val Gln Ile
225                 230                 235                 240 cga aat cat cta aag aat acg gca act agt tta gga agc acg aac ttg     768
Arg Asn His Leu Lys Asn Thr Ala Thr Ser Leu Gly Ser Thr Asn Leu
                245                 250                 255 tat gga agc gga ctt gtt aac gca gaa gcg gca acg cgt                 807
Tyr Gly Ser Gly Leu Val Asn Ala Glu Ala Ala Thr Arg
            260                 265
```

<210> SEQ ID NO 2
<211> LENGTH: 269
<212> TYPE: PRT
<213> ORGANISM: Artificial
<220> FEATURE:
<223> OTHER INFORMATION: Synthetic Construct

<400> SEQUENCE: 2

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asp Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asn Val Gln Ser Thr Tyr Pro Gly Asn Arg Tyr
        195                 200                 205

Val Ser Met Asn Gly Thr Ser Met Ala Thr Pro His Val Ala Gly Val
210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 3
<211> LENGTH: 807
<212> TYPE: DNA
<213> ORGANISM: Artificial
<220> FEATURE:
<223> OTHER INFORMATION: Prepared by DNA-shuffling
<220> FEATURE:
<221> NAME/KEY: CDS
<222> LOCATION: (1)..(807)
<223> OTHER INFORMATION: prepared by DNA shuffling

<400> SEQUENCE: 3

```
gcg caa tcg gta cca tgg gga att agc cgt gtg caa gcc cca gct gcc    48
Ala Gln Ser Val Pro Trp Gly Ile Ser Arg Val Gln Ala Pro Ala Ala
1               5                   10                  15
```

```
cat aac cgt gga ttg aca ggt tct ggt gta aaa gtt gct gtc ctc gat        96
His Asn Arg Gly Leu Thr Gly Ser Gly Val Lys Val Ala Val Leu Asp
             20                  25                  30 aca ggg ata tcc act cat cca gat cta aat att cgt ggt ggc gca agc       144
Thr Gly Ile Ser Thr His Pro Asp Leu Asn Ile Arg Gly Gly Ala Ser
         35                  40                  45 ttt gta cca ggg gaa ccg tcg act caa gat ggg aat ggg cac ggg acg       192
Phe Val Pro Gly Glu Pro Ser Thr Gln Asp Gly Asn Gly His Gly Thr
 50                  55                  60 cac gtt gca gga aca gtg gca gct ctt aat aat tca atc ggt gtg att       240
His Val Ala Gly Thr Val Ala Ala Leu Asn Asn Ser Ile Gly Val Ile
 65                  70                  75                  80 ggt gtg gca cca agt gct gat cta tac gct gta aaa gta ctt gga gca       288
Gly Val Ala Pro Ser Ala Asp Leu Tyr Ala Val Lys Val Leu Gly Ala
                 85                  90                  95 aat ggt aga gga agc gtt agt gga att gct caa ggt cta gag tgg gct       336
Asn Gly Arg Gly Ser Val Ser Gly Ile Ala Gln Gly Leu Glu Trp Ala
            100                 105                 110 gca gcg aat aac atg cat att gct aac atg agt ctc ggt agt gat gca       384
Ala Ala Asn Asn Met His Ile Ala Asn Met Ser Leu Gly Ser Asp Ala
        115                 120                 125 cct agt act aca ctt gag cgt gca gtc aac tac gcg aca agc caa ggt       432
Pro Ser Thr Thr Leu Glu Arg Ala Val Asn Tyr Ala Thr Ser Gln Gly
    130                 135                 140 gta cta gtt att gca gcg act ggt aac aac ggt tcc ggt tca gta ggc       480
Val Leu Val Ile Ala Ala Thr Gly Asn Asn Gly Ser Gly Ser Val Gly
145                 150                 155                 160 tat ccg gcc cgt tat gcg aac gca atg gca gtc gga gct act gat caa       528
Tyr Pro Ala Arg Tyr Ala Asn Ala Met Ala Val Gly Ala Thr Asp Gln
                165                 170                 175 aac aac aac cgc gct agc ttt tca cag tat ggc gca ggc ctt gac att       576
Asn Asn Asn Arg Ala Ser Phe Ser Gln Tyr Gly Ala Gly Leu Asp Ile
            180                 185                 190 gtc gca ccc ggg gta aac gtg cag agc aca tac cca ggt tca aca tat       624
Val Ala Pro Gly Val Asn Val Gln Ser Thr Tyr Pro Gly Ser Thr Tyr
        195                 200                 205 gcc agc tta aac ggt aca tcg atg gct act cct cat gtt gca ggt gcg       672
Ala Ser Leu Asn Gly Thr Ser Met Ala Thr Pro His Val Ala Gly Ala
    210                 215                 220 gcc gcc ctt gtt aaa caa aag aac cca tct tgg tct aat gta caa att       720
Ala Ala Leu Val Lys Gln Lys Asn Pro Ser Trp Ser Asn Val Gln Ile
225                 230                 235                 240 cga aat cat cta aag aat acg gca act agt tta gga agc acg aac ttg       768
Arg Asn His Leu Lys Asn Thr Ala Thr Ser Leu Gly Ser Thr Asn Leu
                245                 250                 255 tat gga agc gga ctt gtt aac gca gaa gcg gca acg cgt                   807
Tyr Gly Ser Gly Leu Val Asn Ala Glu Ala Ala Thr Arg
            260                 265

<210> SEQ ID NO 4
<211> LENGTH: 269
<212> TYPE: PRT
<213> ORGANISM: Artificial
<220> FEATURE:
<223> OTHER INFORMATION: Synthetic Construct

<400> SEQUENCE: 4

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30
```

```
Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
 50                  55                  60

His Val Ala Gly Thr Val Ala Ala Leu Asn Asn Ser Ile Gly Val Ile
 65                  70                  75                  80

Gly Val Ala Pro Ser Ala Asp Leu Tyr Ala Val Lys Val Leu Gly Ala
                 85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
            115                 120                 125

Pro Ser Thr Thr Leu Glu Arg Ala Val Asn Tyr Ala Thr Ser Gln Gly
130                 135                 140

Val Leu Val Ile Ala Ala Thr Gly Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
            210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 5
<211> LENGTH: 275
<212> TYPE: PRT
<213> ORGANISM: Bacillus subtilis

<400> SEQUENCE: 5

Ala Gln Ser Val Pro Tyr Gly Val Ser Gln Ile Lys Ala Pro Ala Leu
 1                   5                  10                  15

His Ser Gln Gly Tyr Thr Gly Ser Asn Val Lys Val Ala Val Ile Asp
             20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
            115                 120                 125

Pro Ser Gly Ser Ala Ala Leu Lys Ala Ala Val Asp Lys Ala Val Ala
130                 135                 140
```

```
Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
    210                 215                 220

Pro His Val Ala Gly Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 6
<211> LENGTH: 269
<212> TYPE: PRT
<213> ORGANISM: Artificial
<220> FEATURE:
<223> OTHER INFORMATION: Prepared by DNA-shuffling

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Val Ala Ala Leu Asn Asn Ser Ile Gly Val Ile
65                  70                  75                  80

Gly Val Ala Pro Ser Ala Asp Leu Tyr Ala Val Lys Val Leu Gly Ala
                85                  90                  95

Asn Gly Arg Gly Ser Val Ser Gly Ile Ala Gln Gly Leu Glu Trp Ala
            100                 105                 110

Ala Ala Asn Asn Met His Ile Ala Asn Met Ser Leu Gly Ser Asp Ala
        115                 120                 125

Pro Ser Thr Thr Leu Glu Arg Ala Val Asn Tyr Ala Thr Ser Gln Gly
    130                 135                 140

Val Leu Val Ile Ala Ala Thr Gly Asn Asn Gly Ser Gly Ser Val Gly
145                 150                 155                 160

Tyr Pro Ala Arg Tyr Ala Asn Ala Met Ala Val Gly Ala Thr Asp Gln
                165                 170                 175

Asn Asn Arg Arg Ala Asn Phe Ser Gln Tyr Gly Thr Gly Ile Asp Ile
            180                 185                 190

Val Ala Pro Gly Val Asp Ile Glu Ser Thr Tyr Pro Gly Ser Ser Tyr
        195                 200                 205

Asp Ser Leu Ser Gly Thr Ser Met Ala Thr Pro His Val Ala Gly Val
    210                 215                 220
```

```
Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```